(12) United States Patent
Hauel et al.

(10) Patent No.: US 8,937,073 B2
(45) Date of Patent: Jan. 20, 2015

(54) DISUBSTITUTED TETRAHYDROFURANYL COMPOUNDS AND THEIR USE AS B1-RECEPTOR ANTAGONISTS

(75) Inventors: Norbert Hauel, Schemmerhofen (DE); Angelo Ceci, Mittelbiberach (DE); Henri Doods, Warthausen (DE); Birgit Jung, Laupheim (DE); Raimund Kuelzer, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/208,567

(22) Filed: Aug. 12, 2011

(65) Prior Publication Data
US 2012/0208823 A1  Aug. 16, 2012

(30) Foreign Application Priority Data

Aug. 20, 2010  (EP) .................................. 10173489

(51) Int. Cl.
C07D 239/26   (2006.01)
C07D 405/12   (2006.01)
C07D 401/12   (2006.01)
C07D 401/14   (2006.01)
C07D 403/12   (2006.01)

(52) U.S. Cl.
CPC ............ C07D 401/12 (2013.01); C07D 401/14 (2013.01); C07D 403/12 (2013.01)
USPC ......... 514/256; 544/335; 546/256; 546/284.7

(58) Field of Classification Search
USPC .............. 544/238, 333, 335; 546/284.7, 256; 514/252.03, 252.01, 256
See application file for complete search history.

(56) References Cited

U.S. PATENT DOCUMENTS

| | | | |
|---|---|---|---|
| 8,372,838 B2 | 2/2013 | Hauel et al. | |
| 8,450,306 B2 | 5/2013 | Hauel et al. | |
| 2006/0173023 A1 | 8/2006 | Wood et al. | |
| 2010/0197664 A1 | 8/2010 | Kauffmann-Hefner et al. | |
| 2010/0240669 A1 | 9/2010 | Hauel et al. | |
| 2011/0263626 A1 | 10/2011 | Hauel et al. | |
| 2012/0015979 A1* | 1/2012 | Moran et al. .................. | 514/314 |
| 2012/0208823 A1 | 8/2012 | Hauel et al. | |
| 2014/0038977 A1 | 2/2014 | Hauel et al. | |

FOREIGN PATENT DOCUMENTS

| | | |
|---|---|---|
| CA | 2790952 A1 | 9/2011 |
| WO | 03065789 A2 | 8/2003 |
| WO | 03066577 A1 | 8/2003 |
| WO | 2004019868 A2 | 3/2004 |
| WO | 2005016886 A1 | 2/2005 |
| WO | 2005085198 A2 | 9/2005 |
| WO | 2008050167 A1 | 5/2008 |
| WO | 2009013299 A2 | 1/2009 |
| WO | 2009021946 A1 | 2/2009 |
| WO | 2009027450 A1 | 3/2009 |
| WO | 2009036996 A2 | 3/2009 |
| WO | 2010057899 A1 | 5/2010 |
| WO | 2010097372 A1 | 9/2010 |
| WO | 2010097374 A1 | 9/2010 |
| WO | 2011104203 A1 | 9/2011 |
| WO | 2012022792 A1 | 2/2012 |
| WO | 2012022793 A1 | 2/2012 |
| WO | 2012022794 A1 | 2/2012 |

(Continued)

OTHER PUBLICATIONS

Kuduk, et al., J. Med. Chem., 2007, 50, 272-282.*

(Continued)

*Primary Examiner* — James O Wilson
*Assistant Examiner* — Cecilia M Jaisle
(74) *Attorney, Agent, or Firm* — Michael P. Morris; Anthony P. Bottino

(57) ABSTRACT

Disubstituted tetrahydrofuranyl compounds of general formula I

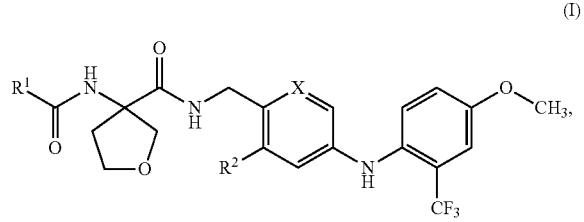

(I)

of which the following are exemplary:

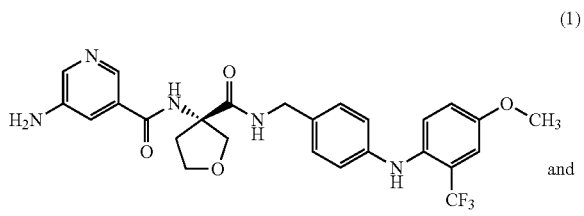

(1)

and

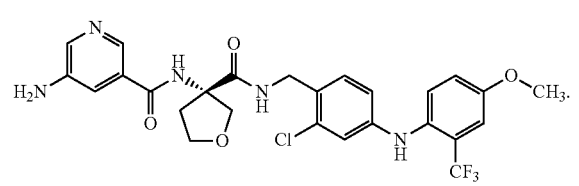

(2)

20 Claims, No Drawings

(56) References Cited

FOREIGN PATENT DOCUMENTS

| | | |
|---|---|---|
| WO | 2012022795 A1 | 2/2012 |
| WO | 2012024559 A1 | 2/2012 |

OTHER PUBLICATIONS

International Search Report, for PCT/ISA/210, and Written Opinion, Form PCT/ISA/237, for cooresponding PCT application PCT/EP2011/064260, date of mailing Nov. 16, 2011.

Entrez Gene: BDKRB1 bradykinin receptor B1 [ *Homo sapiens* (human)], 2011.

B2 Receptor—Mediated Enhanced Bradykinin Sensitivity of Rat Cutaneous C-Fiber Nociceptors During Persistent Inflammation, Ratan Kumar Banik, Yasuko Kozaki, Jun Sato, Lajos Gera and Kazue Mizumura, J Neurophysiol 86:2727-2735, 2001.

Amelioration of hyperalgesia by kinin receptor antagonists or kininogen deficiency in chronic constriction nerve injury in rats, S.Yamaguchi-Sase, I. Hayashi, H. Okamoto,Y. Nara1, S. Matsuzaki, S. Hoka and M. Majima, Inflamm. res. 52 (2003) 164-169.

Antihyperalgesic activity of a novel nonpeptide bradykinin B1 receptor antagonist in transgenic mice expressing the human B1 receptor, Alyson Fox, Satbir Kaur, Bifang Li, Moh Panesar, Uma Saha, Clare Davis, Ilaria Dragoni, Sian Colley, Tim Ritchie, Stuart Bevan, Gillian Burgess & Peter McIntyre, British Journal of Pharmacology (2005) 144, 889-899.

Pharmacological, Pharmacokinetic, and Primate Analgesic Efficacy Profile of the Novel Bradykinin B1 Receptor Antagonist ELN441958, Jon E. Hawkinson, Balazs G. Szoke, Albert W. Garofalo, Dennis S. Hom, Hongbing Zhang, Mark Dreyer, Juri Y. Fukuda, Linda Chen, Bhushan Samant, Stellanie Simmonds, Karla P. Zeitz, Angie Wadsworth, Anna Liao, Raymond A. Chavez, Wes Zmolek, Lany Ruslim, Michael P. Bova, Ryan Holcomb, Eduardo R. Butelman, Mei-Chuan Ko, and Annika B. Malmberg, JPET 322:619-630, 2007.

Abtract, BI 113823, a novel B1 receptor antagonist exhibiting antinociceptive properties in inflammatory pain models, H. Doods1, N. Hauel1, A. Kirsten2, G. Kramer1, A. Ceci1, The 6th World Congress, World Institute of Pain, Feb. 4-12, 2012.

Kaufman et al. Arthritis Research & Therapy 2011, 13:R76.

Abstract in English for WO 2010/097374, Sep. 2, 2010.

\* cited by examiner

DISUBSTITUTED TETRAHYDROFURANYL COMPOUNDS AND THEIR USE AS B1-RECEPTOR ANTAGONISTS

The present invention relates to disubstituted tetrahydrofuranyl compounds of general formula I

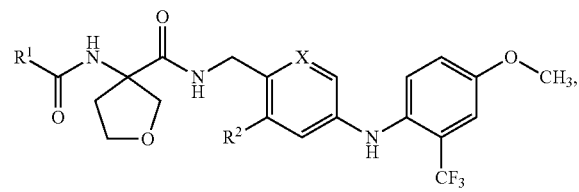

(I)

wherein the variables $R^1$, $R^2$ and X are defined as described hereinafter, the enantiomers, the diastereomers, the mixtures and the salts thereof, particularly the physiologically acceptable salts thereof with organic or inorganic acids or bases, which have valuable properties, processes for preparing them, the medicaments containing the pharmacologically effective compounds as well as the preparation thereof and the use thereof.

BACKGROUND TO THE INVENTION

1. Technical Field

The present invention relates to disubstituted tetrahydrofuranyl compounds and the use thereof as B1-receptor antagonists, pharmaceutical compositions containing these compounds and methods for using them for the prevention or treatment of acute pain, visceral pain, neuropathic pain, inflammatory and pain receptor-mediated pain, tumour pain and headaches.

2. Prior Art

Compounds with a B1-antagonistic activity have already been described in the patent applications WO 2009/027450 and WO 2010/057899.

One aim of the present invention was to provide new compounds which are particularly suitable as pharmacological active substances in medicaments that can be used for the treatment of diseases which are at least partially mediated by the B1 receptor.

DETAILED DESCRIPTION OF THE INVENTION

In the above general formula I, in an embodiment 1 $R^1$ denotes a group selected from

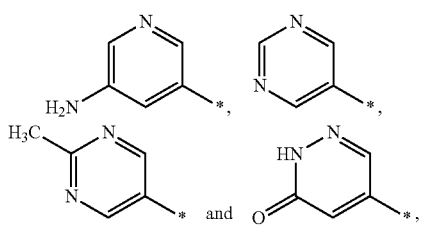

$R^2$ denotes H, Cl or F and
X denotes CH or N,
the enantiomers, the diastereomers, the mixtures and the salts thereof, particularly the physiologically acceptable salts thereof with organic or inorganic acids or bases.

An embodiment 2 of the present invention consists in the compounds of general formula Ia

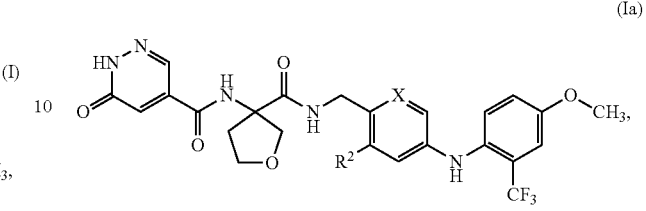

(Ia)

wherein
$R^2$ denotes H, Cl or F and
X denotes CH or N,
the enantiomers, the diastereomers, the mixtures and the salts thereof, particularly the physiologically acceptable salts thereof with organic or inorganic acids or bases.

An embodiment 3 of the present invention consists in the compounds of general formula Ib

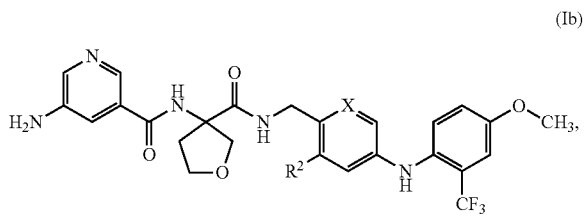

(Ib)

wherein
$R^2$ denotes H, Cl or F and
X denotes CH or N,
the enantiomers, the diastereomers, the mixtures and the salts thereof, particularly the physiologically acceptable salts thereof with organic or inorganic acids or bases.

An embodiment 4 of the present invention consists in the compounds of general formula Ic

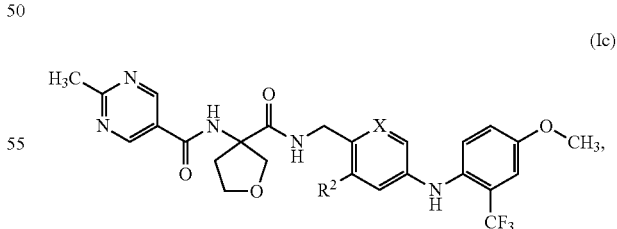

(Ic)

wherein
$R^2$ denotes H, Cl or F and
X denotes CH or N,
the enantiomers, the diastereomers, the mixtures and the salts thereof, particularly the physiologically acceptable salts thereof with organic or inorganic acids or bases.

An embodiment 5 of the present invention consists in the compounds of general formula Id

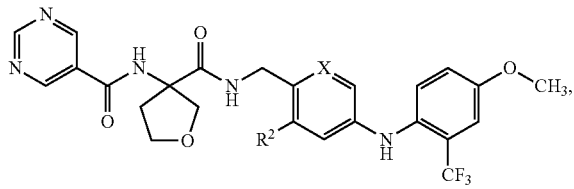

(Id)

wherein

R² denotes H, Cl or F and

X denotes CH or N, the enantiomers, the diastereomers, the mixtures and the salts thereof, particularly the physiologically acceptable salts thereof with organic or inorganic acids or bases.

The following are mentioned as examples of most particularly preferred compounds of the above general formula I:

| No. | Structure |
|---|---|
| (1) | 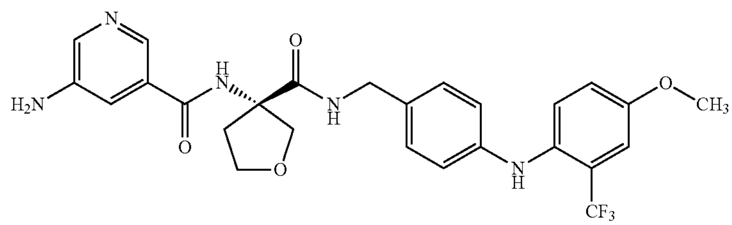 [SMILES: COc1ccc(Nc2ccc(CNC(=O)[C@]3(NC(=O)c4cncc(N)c4)CCOC3)cc2)c(C(F)(F)F)c1] |
| (2) | 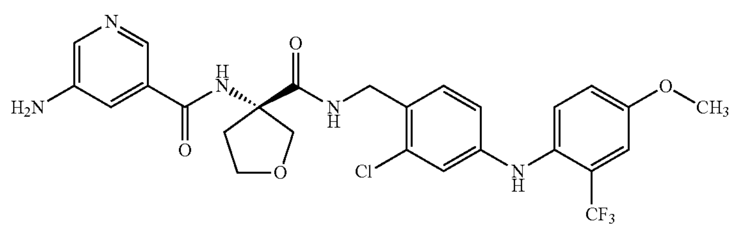 [SMILES: COc1ccc(Nc2ccc(CNC(=O)[C@]3(NC(=O)c4cncc(N)c4)CCOC3)c(Cl)c2)c(C(F)(F)F)c1] |
| (3) | 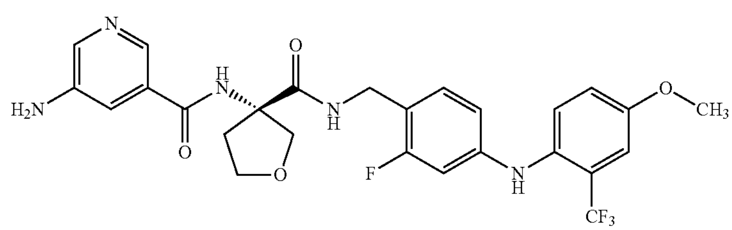 [SMILES: COc1ccc(Nc2ccc(CNC(=O)[C@]3(NC(=O)c4cncc(N)c4)CCOC3)c(F)c2)c(C(F)(F)F)c1] |
| (4) | 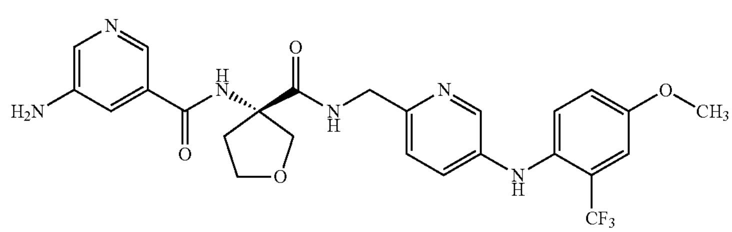 [SMILES: COc1ccc(Nc2ccc(CNC(=O)[C@]3(NC(=O)c4cncc(N)c4)CCOC3)nc2)c(C(F)(F)F)c1] |
| (5) | 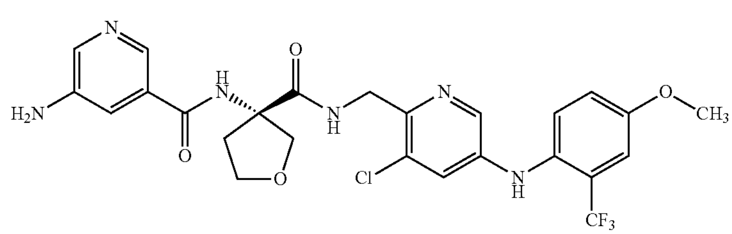 [SMILES: COc1ccc(Nc2cnc(CNC(=O)[C@]3(NC(=O)c4cncc(N)c4)CCOC3)c(Cl)c2)c(C(F)(F)F)c1] |

-continued

| No. | Structure |
|---|---|
| (6) | 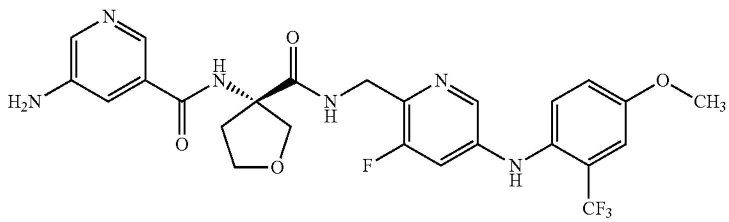 [SMILES: COc1ccc(Nc2cnc(CNC(=O)[C@]3(NC(=O)c4cncc(N)c4)CCOC3)c(F)c2)c(C(F)(F)F)c1] |
| (7) | 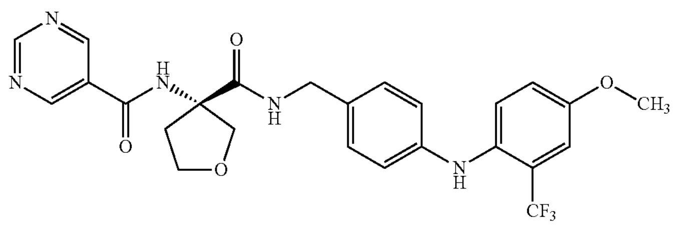 [SMILES: COc1ccc(Nc2ccc(CNC(=O)[C@]3(NC(=O)c4cncnc4)CCOC3)cc2)c(C(F)(F)F)c1] |
| (8) | 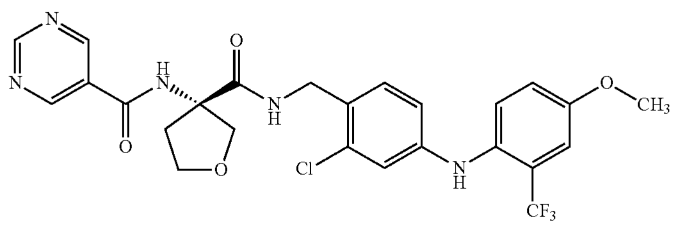 [SMILES: COc1ccc(Nc2ccc(CNC(=O)[C@]3(NC(=O)c4cncnc4)CCOC3)c(Cl)c2)c(C(F)(F)F)c1] |
| (9) | 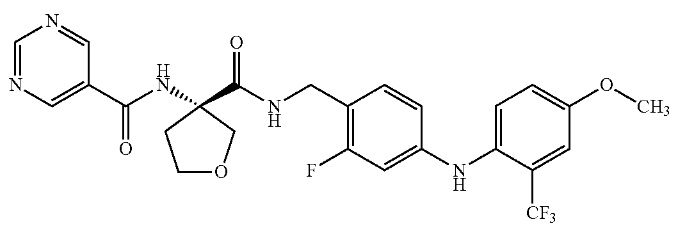 [SMILES: COc1ccc(Nc2ccc(CNC(=O)[C@]3(NC(=O)c4cncnc4)CCOC3)c(F)c2)c(C(F)(F)F)c1] |
| (10) | 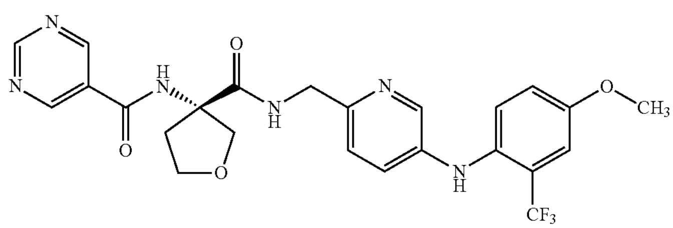 [SMILES: COc1ccc(Nc2ccc(CNC(=O)[C@]3(NC(=O)c4cncnc4)CCOC3)nc2)c(C(F)(F)F)c1] |
| (11) | 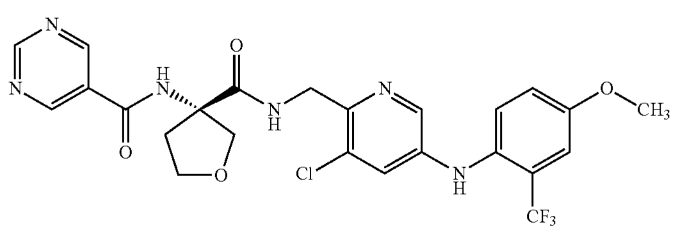 [SMILES: COc1ccc(Nc2cnc(CNC(=O)[C@]3(NC(=O)c4cncnc4)CCOC3)c(Cl)c2)c(C(F)(F)F)c1] |
| (12) | 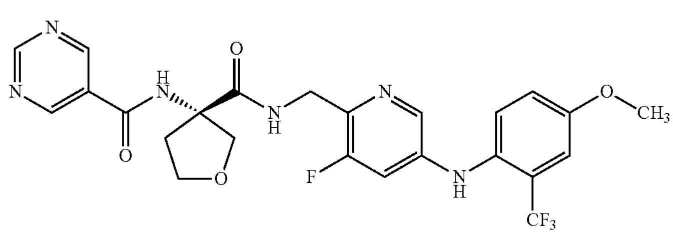 [SMILES: COc1ccc(Nc2cnc(CNC(=O)[C@]3(NC(=O)c4cncnc4)CCOC3)c(F)c2)c(C(F)(F)F)c1] |

-continued

| No. | Structure |
|---|---|
| (13) | 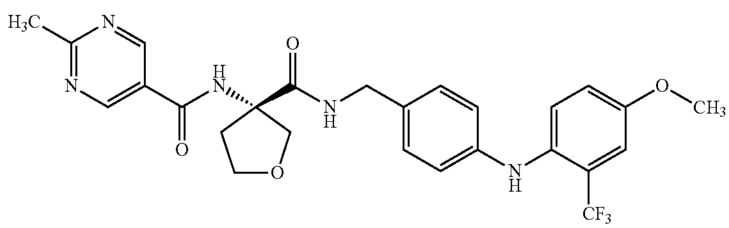 |
| (14) | 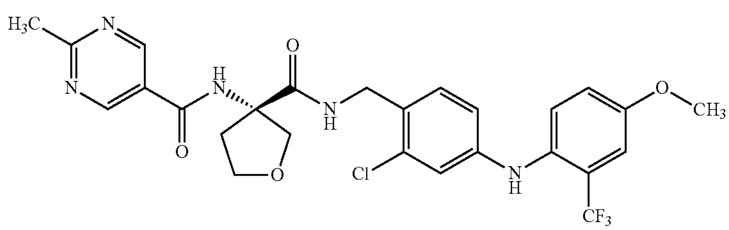 |
| (15) | 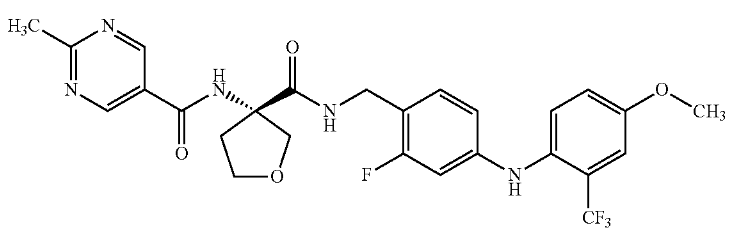 |
| (16) | 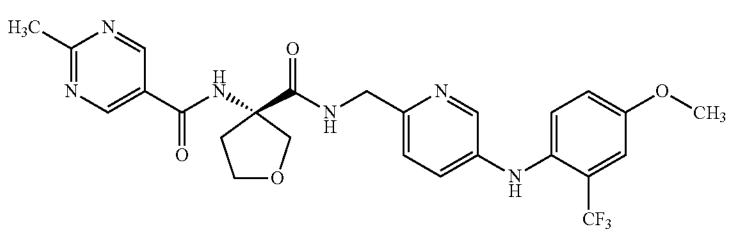 |
| (17) | 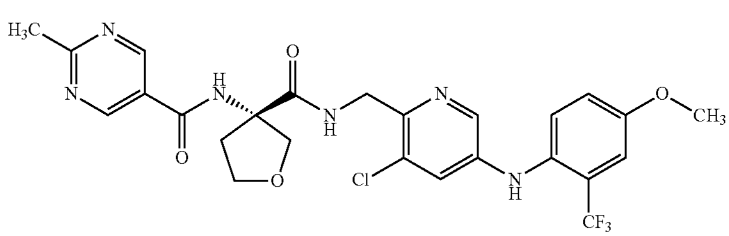 |
| (18) | 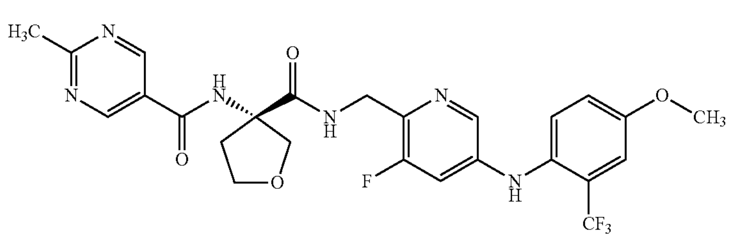 |
| (19) | 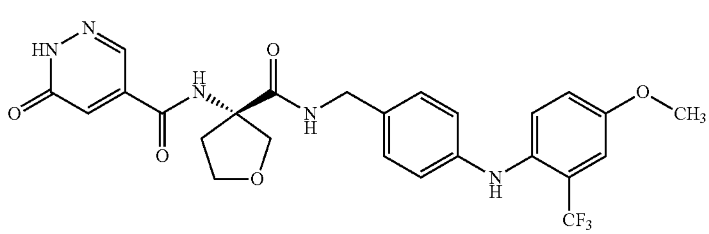 [SMILES: COc1ccc(Nc2ccc(CNC(=O)[C@]3(NC(=O)c4cn[nH]c(=O)c4)CCOC3)cc2)c(C(F)(F)F)c1] |

| No. | Structure |
|---|---|
| (20) | 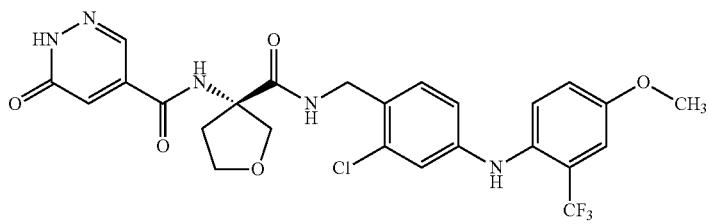 [SMILES: COc1ccc(Nc2ccc(CNC(=O)[C@]3(NC(=O)c4cn[nH]c(=O)c4)CCOC3)c(Cl)c2)c(C(F)(F)F)c1] |
| (21) | 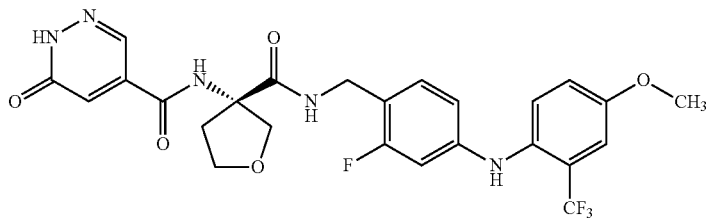 [SMILES: COc1ccc(Nc2ccc(CNC(=O)[C@]3(NC(=O)c4cn[nH]c(=O)c4)CCOC3)c(F)c2)c(C(F)(F)F)c1] |
| (22) | 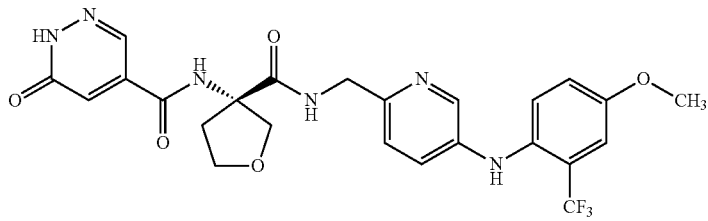 [SMILES: COc1ccc(Nc2ccc(CNC(=O)[C@]3(NC(=O)c4cn[nH]c(=O)c4)CCOC3)nc2)c(C(F)(F)F)c1] |
| (23) | 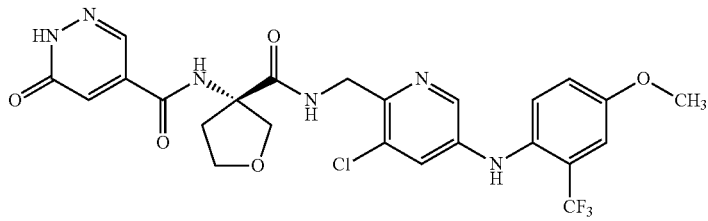 [SMILES: COc1ccc(Nc2cnc(CNC(=O)[C@]3(NC(=O)c4cn[nH]c(=O)c4)CCOC3)c(Cl)c2)c(C(F)(F)F)c1] |
| (24) | 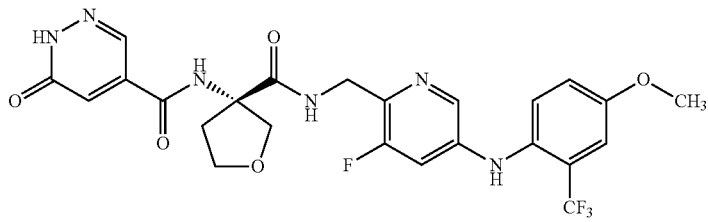 [SMILES: COc1ccc(Nc2cnc(CNC(=O)[C@]3(NC(=O)c4cn[nH]c(=O)c4)CCOC3)c(F)c2)c(C(F)(F)F)c1] | the enantiomers, the diastereomers, the mixtures and the salts thereof, particularly the physiologically acceptable salts thereof with organic or inorganic acids or bases.

TERMS AND DEFINITIONS USED

The subject-matter of this invention encompasses the novel compounds of general formula I as mentioned hereinbefore, including the salts thereof, wherein one or more hydrogen atoms, for example one, two, three, four or five hydrogen atoms, are replaced by deuterium.

Unless stated otherwise, a chemical formula or a name specified in the description or in a claim encompasses not only all the structurally possible and thermodynamically stable tautomers but also all the stereoisomers, optical isomers, geometric isomers (e.g. enantiomers, diastereomers, E/Z isomers, etc.), racemates and mixtures of different proportions of the individual enantiomers, mixtures of diastereomers or mixtures of each form mentioned hereinbefore in which isomers and enantiomers exist.

Also covered by the subject-matter of the invention are solvates of the compounds of general formula I, for example the hydrates thereof.

Also included in the subject-matter of the invention are the salts of the compounds mentioned in each case, including the physiologically acceptable salts, as well as the solvates thereof, such as the hydrates, for example.

Compounds of general formula I, if they contain suitable basic functions, for example amino groups, may be converted into the physiologically acceptable salts thereof with inorganic or organic acids, particularly for pharmaceutical applications.

The term "physiologically acceptable salt" as used in the present invention is preferably taken to mean salts of the compounds according to the invention which are physiologically acceptable, i.e. which are particularly suitable for use in humans and/or mammals.

The term "physiologically acceptable" is used in the present invention to refer to those compounds, ingredients, compositions and/or preparations which are deemed suitable for use in contact with human or animal tissue within the scope of a reasonable medical judgment, without excessive toxicity, irritation, allergic reactions or other problems or complications, and which correspond to a proportionate risk/benefit ratio.

Examples of inorganic acids for this purpose include for example hydrobromic acid, phosphoric acid, nitric acid, hydrochloric acid or sulphuric acid, while examples of organic acids include formic acid, malic acid, ascorbic acid, benzoic acid, succinic acid, acetic acid, ethylenediaminetetraacetic acid, fumaric acid, glutamic acid, hexane-1-sulphonic acid, carbonic acid, maleic acid, mandelic acid, lactic acid, monomethylsebacic acid, nicotinic acid, oxalic acid, 5-oxoproline, saccharinic acid, sulphonic acids, such as for example methanesulphonic acid, camphorsulphonic acid, ethanesulphonic acid, ethane-1,2-disulphonic acid, benzenesulphonic acid or p-toluenesulphonic acid, tartaric acid or citric acid (cf. "Pharmaceutical salts", Birge, S. M. et al., J. Pharm. Sci., (1977), 66, 1-19).

Moreover, the compounds of general formula I, if they contain suitable carboxylic acid functions, may be converted into the physiologically acceptable salts thereof with inorganic or organic bases, particularly for pharmaceutical applications. Examples of inorganic bases include for example alkali metal or alkaline earth metal hydroxides, for example sodium hydroxide or potassium hydroxide, or carbonates, ammonia, zinc or ammonium hydroxides; examples of organic amines include diethylamine, triethylamine, ethanolamine, diethanolamine, triethanolamine, cyclohexylamine or dicyclohexylamine.

The physiologically acceptable salts according to the present invention may be synthesised starting from the compounds according to the invention which contain a suitable basic or acid unit, using conventional chemical methods. Generally, salts of this kind may be prepared by reacting the free acid or base group with the required amount of base or acid in water or an organic solvent, such as for example diethyl ether, ethyl acetate, ethanol, isopropanol, acetonitrile or a mixture of these solvents.

The compounds according to the invention may occur as racemates if they have only one chiral element, but they may also be obtained as pure enantiomers, i.e. in the (R) or (S) form.

However, the application also encompasses the individual diastereomeric pairs of antipodes or the mixtures thereof which are present when there is more than one chiral element in the compounds of general formula I, as well as the individual optically active enantiomers of which the above-mentioned racemates are made up.

Compounds with a carbon double bond may be present in both the E and Z form.

If a compound may be present in different tautomeric forms, the compound prepared is not restricted to one tautomeric form but includes all tautomeric forms. This also applies particularly to nitrogen-containing heteroaryls:

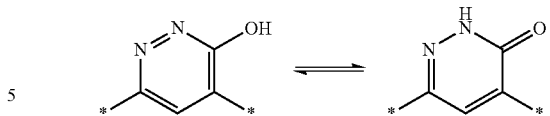

Methods of Preparation

According to the invention the compounds of general formula I are obtained using methods known per se, for example by the following methods:

(A) Amide Coupling:

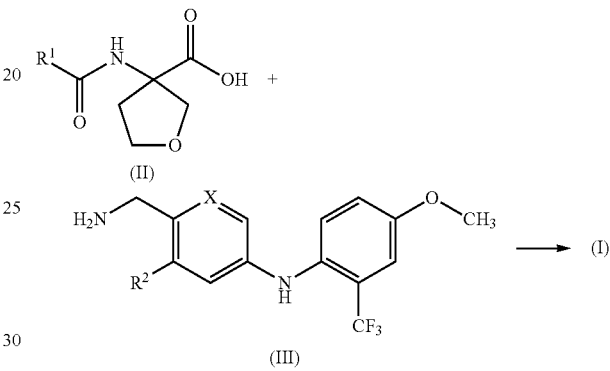

The illustrated linking of carboxylic acids of general formula II, wherein $R^1$ is as hereinbefore defined, with amines of general formula III, wherein $R^2$ and X are as hereinbefore defined, to form carboxylic acid amides of general formula I wherein $R^1$, $R^2$ and X are as hereinbefore defined, may be carried out by conventional methods of amide formation.

The coupling is preferably carried out using methods known from peptide chemistry (cf. for example Houben-Weyl, Methoden der Organischen Chemie, vol. 15/2), using for example carbodiimides such as e.g. dicyclohexylcarbodiimide (DCC), diisopropylcarbodiimide (DIC) or ethyl-(3-dimethylamino-propyl)-carbodiimide, O-(1H-benzotriazol-1-yl)-N,N—N',N'-tetramethyluronium-hexafluorophosphate (HBTU) or -tetrafluoroborate (TBTU) or 1H-benzotriazol-1-yl-oxy-tris-(dimethylamino)-phosphonium-hexafluorophosphate (BOP). The speed of the reaction may be increased by the addition of 1-hydroxybenzotriazole (HOBt) or 3-hydroxy-4-oxo-3,4-di-hydro-1,2,3-benzotriazine (HOObt). The couplings are normally carried out with equimolar amounts of the coupling components and the coupling reagent in solvents such as dichloromethane, tetrahydrofuran (THF), acetonitrile, dimethylformamide (DMF), dimethylacetamide (DMA), N-methylpyrrolidone (NMP) or mixtures thereof. If necessary, an auxiliary base such as, for example, diisopropylethylamine (DIPEA, Hünig base) is additionally used.

It is also possible to convert the carboxylic acids of general formula II, wherein $R^1$ is as hereinbefore defined, into the corresponding carboxylic acid chlorides and then react the latter with amines of general formula III, wherein $R^2$ and X are as hereinbefore defined. Carboxylic acid chlorides are synthesised by methods known from the literature (cf. for example Houben-Weyl, Methoden der Organischen Chemie, vol. E5/1).

(B) Reduction of the Nitrile Group:

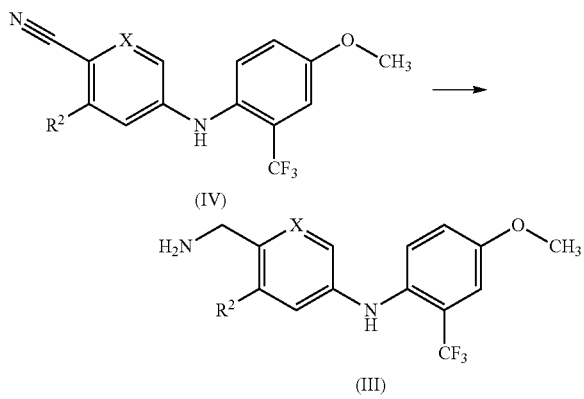

The reduction of a nitrile of general formula IV, wherein $R^2$ and X are as hereinbefore defined, to obtain an amine of general formula III, wherein $R^2$ and X are as hereinbefore defined, may be carried out under standard conditions of catalytic hydrogenolysis with a catalyst, such as for example Raney nickel, in a solvent, such as for example ammoniacal methanol or ethanol, or with a reducing agent, such as for example lithium aluminium hydride or sodium borohydride, in a solvent, such as for example tetrahydrofuran, optionally in the presence of a Lewis acid such as aluminium chloride.

(C) Nucleophilic Aromatic Substitution or Transition Metal-Catalysed Coupling:

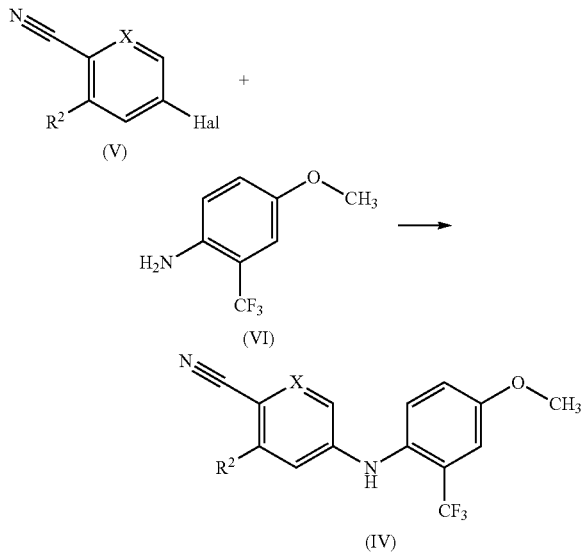

The reaction of the aniline VI with a nitrile of general formula V, wherein $R^2$ and X are as hereinbefore defined and Hal denotes a fluorine, chlorine or bromine atom, is carried out by known methods, for example without solvent or in a solvent such as tetrahydrofuran, dimethylformamide or dimethylsulphoxide and conveniently in the presence of a base, such as for example triethylamine, sodium hydroxide solution or potassium carbonate, at a temperature of 20° C. to 160° C.

An alternative method of preparing compounds of general formula IV is the palladium-catalysed reaction of a nitrile of general formula V, wherein Hal denotes chlorine, bromine or iodine, with the aniline VI. Reaction conditions for this reaction, also known as the Buchwald-Hartwig reaction, are known from the literature.

Description of the Method of Binding the cynoBK1-Receptor

CHO cells that express the cynomolgus B1 receptor are cultivated in "HAM'S F-12 Medium". The medium is removed from confluent cultures, the cells are washed with PBS buffer, scraped off or detached using Versene and isolated by centrifuging. Then the cells are homogenised in suspension, the homogenate is centrifuged and resuspended. After the protein content has been determined 200 µl of the homogenate (50 to 250 µg protein/assay) are incubated for 60-180 minutes at ambient temperature with 0.5 to 5.0 nM kallidine (DesArg10,Leu9), [3,4-Prolyl-3,43H(N)] and increasing concentrations of the test substance in a total volume of 250 µl. The incubation is stopped by rapid filtration through GF/B glass fibre filters that have been pre-treated with polyethyleneimine (0.3%). The radioactivity bound to the protein is measured with a TopCount NXT. The radioactivity bound in the presence of 1.0 µM kallidine (DesArg10) is defined as non-specific binding. The concentration binding curve may be analysed using computer-aided non-linear curve fitting to determine the corresponding $K_i$ value for the test substance.

Test Results of the cynoBK1-Receptor Binding Assay:

| Example No. | $K_i$ [nM] |
| --- | --- |
| (1) | 1.0 |
| (3) | 4.7 |
| (4) | 3.6 |
| (6) | 18 |
| (21) | 1.6 |

Indications

In view of their pharmacological properties, the novel compounds and their physiologically acceptable salts are suitable for treating diseases and symptoms of diseases caused at least to some extent by stimulation of bradykinin-B1 receptors, or in which antagonisation of the of bradykinin-B1 receptor can bring about an improvement in symptoms.

In a further aspect the present invention encompasses the compounds of the above-mentioned general formula I according to the invention for use as medicaments.

In view of their pharmacological effect the substances are suitable for the treatment of (a) acute pain such as for example toothache, peri- and post-operative pain, traumatic pain, muscle pain, the pain caused by burns, sunburn, trigeminal neuralgia, pain caused by colic, as well as spasms of the gastro-intestinal tract or uterus;

(b) visceral pain such as for example chronic pelvic pain, gynaecological pain, pain before and during menstruation, pain caused by pancreatitis, peptic ulcers, interstitial cystitis, renal colic, cholecystitis, prostatitis, angina pectoris, pain caused by irritable bowel, non-ulcerative dyspepsia and gastritis, prostatitis, non-cardiac thoracic pain and pain caused by myocardial ischaemia and cardiac infarct;

(c) neuropathic pain such as for example painful polyneuropathies, pain of diabetic neuropathy, AIDS-associated neuropathic pain, non-herpes-associated neuralgia, post-zoster neuralgia, nerve damage, cerebro-cranial trauma, pain of nerve damage caused by toxins or chemotherapy, phantom pain, pain of multiple sclerosis, nerve root tears and painful traumatically-caused damage to individual nerves, and central pain such as for example pain after stroke, spinal injuries or tumours;

d) inflammatory/pain receptor-mediated pain in connection with diseases such as for example osteoarthritis, rheumatoid arthritis, rheumatic fever, tendo-synovitis, bursitis, tendonitis, gout and gout-arthritis, traumatic arthritis, vulvodynia, damage to and diseases of the muscles and fascia, juvenile arthritis, spondylitis, psoriasis-arthritis, myositides, dental disease, influenza and other viral infections such as colds, systemic lupus erythematodes or pain caused by burns, (e) tumour pain associated with cancers such as for example lymphatic or myeloid leukaemia, Hodgkin's disease, non-Hodgkin's lymphomas, lymphogranulomatosis, lymphosarcomas, solid malignant tumours and extensive metastases;

(f) headache diseases of various origins, such as for example cluster headaches, migraine (with or without aura) and tension headaches.

(g) painful conditions of mixed origin, such as for example chronic back pain including lumbago, or fibromyalgia.

The compounds are also suitable for treating (h) inflammatory and/or oedematous diseases of the skin and mucous membranes, such as for example allergic and non-allergic dermatitis, atopic dermatitis, psoriasis, burns, sunburn, bacterial inflammations, irritations and inflammations triggered by chemical or natural substances (plants, insects, insect bites), itching; inflammation of the gums, oedema following trauma caused by burns, angiooedema or uveitis;

(i) inflammatory changes connected with diseases of the airways and lungs such as bronchial asthma, including allergic asthma (atopic and non-atopic) as well as bronchospasm on exertion, occupationally induced asthma, viral or bacterial exacerbation of an existing asthma and other non-allergically induced asthmatic diseases; chronic bronchitis and chronic obstructive pulmonary disease (COPD) including pulmonary emphysema, viral or bacterial exacerbation of chronic bronchitis or chronic obstructive bronchitis, acute adult respiratory distress syndrome (ARDS), bronchitis, lung inflammation, allergic rhinitis (seasonal and all year round) vasomotor rhinitis and diseases caused by dust in the lungs such as aluminosis, anthracosis, asbestosis, chalicosis, siderosis, silicosis, tabacosis and byssinosis, exogenous allergic alveolitis, pulmonary fibrosis, bronchiectasis, pulmonary diseases in alpha1-antitrypsin deficiency and cough;

(j) inflammatory diseases of the gastrointestinal tract including Crohn's disease and ulcerative colitis, irritable bowel syndrome, pancreatitis;

(k) diabetes mellitus and its effects (such as e.g. diabetic vasculopathy, diabetic neuropathy, diabetic retinopathy) and diabetic symptoms in insulitis (for example hyperglycaemia, diuresis, proteinuria and increased renal excretion of nitrite and kallikrein);

(l) sepsis and septic shock after bacterial infections or after trauma;

(m) inflammatory diseases of the joints and connective tissue such as vascular diseases of the connective tissue, sprains and fractures, and musculoskeletal diseases with inflammatory symptoms such as acute rheumatic fever, polymyalgia rheumatica, reactive arthritis, rheumatoid arthritis, spondylarthritis, and also osteoarthritis, and inflammation of the connective tissue of other origins, and collagenoses of all origins such as systemic lupus erythematodes, scleroderma, polymyositis, dermatomyositis, Sjögren syndrome, Still's disease or Felty syndrome; as well as vascular diseases such as panarteriitis nodosa, polyarthritis nodosa, periarteriitis nodosa, arteriitis temporalis, Wegner's granulomatosis, giant cell arteriitis, arteriosclerosis and erythema nodosum;

(n) diseases of and damage to the central nervous system such as for example cerebral oedema and the treatment and prevention of psychiatric diseases such as depression, for example, and for the treatment and prevention of epilepsy;

(o) disorders of the motility or spasms of respiratory, genito-urinary, gastro-intestinal including biliary or vascular structures and organs;

(p) post-operative fever;

(q) for the treatment and prevention of cardiovascular diseases such as for example high blood pressure and related complaints;

(r) for the treatment and prevention of arteriosclerosis and related complaints;

(s) for the treatment and prevention of cancer and related complaints;

(t) for the treatment and prevention of diseases of the genito-urinary tract such as for example urinary incontinence and related complaints, benign prostatic hyperplasia and hyperactive bladder, nephritis, cystitis (interstitial cystitis);

(u) for the treatment and prevention of morbid obesity and related complaints.

The substances are suitable for causal treatment in the sense of slowing down or stopping the progress of chronically progressive diseases, particularly osteoarthritis, rheumatoid arthritis and spondylarthritis.

In another aspect the present invention encompasses the use of the compounds of the above-mentioned general formula I according to the invention for preparing a medicament for therapeutic use in the above-mentioned indications.

Preferably, the compounds of general formula I according to the invention are used for the treatment of osteoarthritis, rheumatoid arthritis or COPD.

Preferably the novel compounds of general formula I are also used for the treatment of inflammatory diseases of the skin, such as for example allergic and non-allergic dermatitis, atopic dermatitis, psoriasis, burns, sunburn, bacterial inflammations, irritations and inflammations triggered by chemical or natural substances (plants, insects, insect bites) or itching.

The term "treatment" or "therapy" refers to a therapeutic treatment of patients with a manifest, acute or chronic indication, including on the one hand symptomatic (palliative) treatment to relieve the symptoms of the disease and on the other hand causal or curative treatment of the indication with the aim of ending the pathological condition, reducing the severity of the pathological condition or delaying the progression of the pathological condition, depending on the nature or gravity of the indication.

The present invention further relates to the use of a compound of general formula I for preparing a medicament for the acute and prophylactic treatment of acute pain, visceral pain, neuropathic pain, inflammatory/pain receptor-mediated pain, tumour pain, headache pain and pain of mixed causes and other diseases as mentioned above. This use is characterised in that it comprises administering an effective amount of a compound of general formula I or a physiologically acceptable salt thereof to a patient requiring such treatment.

The term "patient" preferably refers to a human being.

In addition to their suitability as therapeutic drugs for humans, these substances are also useful in the veterinary medical treatment of domestic pets, exotic animals and farmed animals.

The present invention further relates to medicaments containing at least one novel compound of general formula I and optionally suitable additives and/or adjuvants and/or optionally other active substances.

The dosage required to achieve a pain-relieving effect varies depending on the weight of the patient, the method of administration, the indication and severity of the complaint. Normally, the amount of active substance to be given is 0.01 to 3 mg/kg body weight, preferably 0.1 to 1 mg/kg, when administered intravenously, and 0.1 to 8 mg/kg body weight, preferably 0.5 to 3 mg/kg, when administered orally, in each case once to three times a day.

The medicaments according to the invention optionally contain, in addition to at least one compound of general formula I according to the invention, suitable inert additives and/or adjuvants, such as for example carrier materials, fillers, solvents, diluents, colourings and/or binders. They may be given as liquid medicines in the form of injectable solutions, drops or syrups, as semi-solid preparations in the form of granules, tablets, pellets, patches, capsules, plasters/spray-on plasters or aerosols.

The compounds prepared according to the invention may be administered by intravenous, subcutaneous, intramuscular, intrarectal or intranasal route, by inhalation, by transdermal or oral route, perorally, parenterally, intradermally, by mouth, rectally or topically, for example to the skin, mucous membranes or into the eyes, while aerosol formulations are particularly suitable for inhalation. They may optionally be incorporated, together with one or more inert conventional carriers and/or diluents, e.g. with maize starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearylalcohol, carboxymethylcellulose or fatty substances such as hard fat or suitable mixtures thereof, into conventional galenic preparations such as tablets, coated tablets, capsules, granules, drops, elixirs, syrups, powders, suspensions, solutions, metered-dose aerosols or suppositories.

Combinations

For treating pain, it may be advantageous to combine the compounds according to the invention with stimulating substances such as caffeine or other pain-alleviating active compounds. If active compounds suitable for treating the cause of the pain are available, these can be combined with the compounds according to the invention.

The following compounds may be used for combination therapy, for example:

Non-steroidal antirheumatics (NSAR) such as for example propionic acid derivatives which may be selected from among alminoprofen, bucloxic acid, carprofen, fenoprofen, ibuprofen, ketoprofen, naproxen, oxaprozin, pirprofen, pranoprofen and tiaprofenic acid; acetic acid derivatives which may be selected from among indomethacin, acemetacin, alclofenac, isoxepac, sulindac and tolmetin; fenamic derivatives which may be selected from among meclofenamic acid, mefenamic acid and tolfenamic acid; biphenyl-carboxylic acid derivatives; oxicams which may be selected from among meloxicam, piroxicam and tenoxicam; salicylic acid derivatives which may be selected from among acetylsalicylic and sulphasalazine; pyrazolones which may be selected from among apazone and feprazone; and coxibs which may be selected from among celecoxib and etoricoxib.

Opiate receptor agonists which may for example be selected from among morphine, Darvon, tramadol and buprenorphine;

Cannabinoid agonists such as for example GW-1000;

Sodium channel blockers which may for example be selected from among carbamazepine, mexiletin, pregabalin, tectin and ralfinamide.

N-type calcium channel blockers such as for example ziconotide.

Serotonergic and noradrenergic modulators which may be selected from among for example duloxetine and amitriptyline.

Corticosteroids which may be selected from among for example betamethasone, budesonide, cortisone, dexamethasone, hydrocortisone, methylprednisolone, prednisolone, prednisone and triamcinolone.

Histamine H1-receptor antagonists which may for example be selected from among bromopheniramine, chloropheniramine, dexchlorpheniramine, triprolidine, clemastine, diphenhydramine, diphenylpyraline, tripelennamine, hydroxyzine, promethazine, trimeprazine azatadine, cyproheptadine, antazoline, pheniramine, pyrilamine, loratadine, cetirizine, desloratadine, fexofenadine and levocetirizine.

Leukotriene antagonists and 5-lipoxygenase inhibitors which may for example be selected from among zafirlukast, montelukast, pranlukast and zileuton.

Local anaesthetics which may for example be selected from among ambroxol and lidocaine.

TRVP1 antagonists which may for example be selected from among AZD-1386, JTS-653 and PHE-377.

Nicotine receptor agonists such as for example A-366833.

P2X3-receptor antagonists such as e.g. A-317491.

anti-NGF antibodies and NGF antagonists which may for example be selected from among JNJ-42160443 and PPH 207.

NK1 and NK2 antagonists such as e.g. CP-728663.

NMDA antagonists which may for example be selected from among CNS-5161, AZ-756 and V-3381.

Potassium channel modulators such as e.g. CL-888.

GABA modulators such as e.g. baclofen.

Anti-migraine drugs such as e.g. sumatriptan, zolmitriptan, naratriptan and eletriptan.

For treating one or more of the above-mentioned respiratory complaints it may be advantageous to combine the compounds of general formula I according to the invention with other active substances for treating respiratory complaints. If suitable active substances for treating the cause of the respiratory complaints are available, these may be combined with the compounds according to the invention.

The compounds of general formula I may optionally also be used in conjunction with other pharmacologically active substances. It is preferable to use active substances of the type selected from among the betamimetics, anticholinergics, corticosteroids, PDE4-inhibitors, LTD4-receptor antagonists, inhibitors of MAP kinases, EGFR-inhibitors, H1-receptor antagonists, H4-receptor antagonists, PAF-antagonists, PI3-kinase inhibitors, CXCR1 and/or CXCR2 receptor antagonists and anti-tussives.

Betamimetics used according to the invention are preferably compounds selected from among arformoterol, carmoterol, formoterol, indacaterol, salmeterol, albuterol, bambuterol, bitolterol, broxaterol, carbuterol, clenbuterol, fenoterol, hexoprenaline, ibuterol, isoetharin, isoprenaline, levosalbutamol, mabuterol, meluadrine, metaproterenol, milveterol, orciprenaline, pirbuterol, procaterol, reproterol, rimiterol, ritodrine, salmefamol, soterenol, sulphonterol, terbutalin, tiaramide, tolubuterol and zinterol or 6-hydroxy-8-{1-hydroxy-2-[2-(4-methoxy-phenyl)-1,1-dimethyl-ethylamino]-ethyl}-4H-benzo[1,4]oxazin-3-one, 8-{2-[2-(2,4-difluoro-phenyl)-1,1-dimethyl-ethylamino]-1-hydroxy-ethyl}-6-hydroxy-4H-benzo[1,4]oxazin-3-one, 8-{2-[2-(3,5-difluoro-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one,
8-{2-[2-(4-fluoro-phenyl)-1,1-dimethyl-ethylamino]-1-hydroxy-ethyl}-6-hydroxy-4H-benzo[1,4]oxazin-3-one,
N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide,
N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide,
N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide,
N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide,
8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one,
8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one,
8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one,
8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one,
N-[2-hydroxy-5-((1R)-1-hydroxy-2-{2-[4-(2-hydroxy-2-phenyl-ethylamino)-phenyl]-ethylamino}-ethyl)-phenyl]-formamide,
8-hydroxy-5-((1R)-1-hydroxy-2-{2-[4-(6-methoxy-biphenyl-3-ylamino)-phenyl]-ethylamino}-ethyl)-1H-quinolin-2-one,
8-hydroxy-5-[(1R)-1-hydroxy-2-(6-phenethylamino-hexylamino)-ethyl]-1H-quinolin-2-one,
5-[(1R)-2-(2-{4-[4-(2-amino-2-methyl-propoxy)-phenylamino]-phenyl}-ethylamino)-1-hydroxy-ethyl]-8-hydroxy-1H-quinolin-2-one,
[3-(4-{6-[(2R)-2-hydroxy-2-(4-hydroxy-3-hydroxymethyl-phenyl)-ethylamino]-hexyloxy}-butyl)-5-methyl-phenyl]-urea,
4-((1R)-2-{6-[2-(2,6-dichloro-benzyloxy)-ethoxy]-hexylamino}-1-hydroxy-ethyl)-2-hydroxymethyl-phenol,
3-(4-{6-[(2R)-2-hydroxy-2-(4-hydroxy-3-hydroxymethyl-phenyl)-ethylamino]-hexyloxy}-butyl)-benzenesulphonamide,
3-(3-{7-[(2R)-2-hydroxy-2-(4-hydroxy-3-hydroxymethyl-phenyl)-ethylamino]-heptyloxy}-propyl)-benzenesulphonamide,
4-((1R)-2-{6-[4-(3-cyclopentanesulphonyl-phenyl)-butoxy]-hexylamino}-1-hydroxy-ethyl)-2-hydroxymethyl-phenol,
N-1-Adamantanyl-2-{3-[(2R)-2-({(2R)-2-hydroxy-2-[4-hydroxy-3-(hydroxymethyl)-phenyl]ethyl}amino)propyl]phenyl}acetamide,
(1R)-5-{2-[6-(2,2-difluoro-2-phenyl-ethoxy)-hexylamino]-1-hydroxy-ethyl}-8-hydroxy-1H-quinolin-2-one
(R,S)-4-(2-{[6-(2,2-difluoro-4-phenylbutoxy)hexyl]amino}-1-hydroxy-ethyl)-2-(hydroxyl-methyl)phenol,
(R,S)-4-(2-{[6-(2,2-difluoro-2-phenylethoxy)hexyl]amino}-1-hydroxy-ethyl)-2-(hydroxymethyl)phenol,
(R,S)-4-(2-{[4,4-difluoro-6-(4-phenylbutoxy)hexyl]amino}-1-hydroxy-ethyl)-2-(hydroxymethyl)phenol,
(R,S)-4-(2-{[6-(4,4-difluoro-4-phenylbutoxy)hexyl]amino}-1-hydroxy-ethyl)-2-(hydroxyl-methyl)phenol,
(R,S)-5-(2-{[6-(2,2-difluoro-2-phenylethoxy)hexyl]amino}-1-hydroxy-ethyl)-8-hydroxyquinolin-2(1H)-one,
(R,S)-[2-({6-[2,2-difluoro-2-(3-methylphenyl)ethoxy]hexyl}amino)-1-hydroxyethyl]-2-(hydroxymethyl)phenol,
4-(1R)-2-{[6-(2,2-difluoro-2-phenylethoxy)hexyl]amino}-1-hydroxyethyl)-2-(hydroxyl-methyl)phenol,
(R,S)-2-(hydroxymethyl)-4-(1-hydroxy-2-{[4,4,5|5-tetrafluoro-6-(3-phenylpropoxy)-hexyl]amino}ethyl)phenol,
(R,S)-5-(2-{[6-(2,2-difluoro-2-phenylethoxy)hexyl]amino}-1-hydroxy-ethyl)-2-hydroxy-phenyl]formamide,
(R,S)-4-[2-({6-[2-(3-bromophenyl)-2,2-difluoroethoxy]hexyl}amino)-1-hydroxyethyl]-2-(hydroxymethyl)phenol,
(R,S)—N-[3-(1,1-difluoro-2-{[6-({2-hydroxy-2-[4-hydroxy-3-(hydroxymethyl)phenyl]-ethyl}amino)hexyl]oxy}ethyl)phenyl]-urea,
3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidin-2,4-dione,
(R,S)-4-[2-({6-[2,2-difluoro-2-(3-methoxyphenyl)ethoxy]hexyl}amino)-1-hydroxyethyl]-2-(hydroxymethyl)phenol,
5-((1R)-2-{[6-(2,2-difluoro-2-phenylethoxy)hexyl]amino}-1-hydroxyethyl)-8-hydroxyquinolin-2(1H)-one,
4-((1R)-2-{[4,4-difluoro-6-(4-phenylbutoxy)hexyl]amino}-1-hydroxy-ethyl)-2-(hydroxyl-methyl)phenol,
(R,S)-4-(2-{[6-(3,3-difluoro-3-phenylpropoxy)hexyl]amino}-1-hydroxy-ethyl)-2-(hydroxylmethyl)phenol,
(R,S)-(2-{[6-(2,2-difluoro-2-phenylethoxy)-4,4-difluorohexyl]amino}-1-hydroxyethyl)-2-(hydroxymethyl)phenol,
(R,S)-4-(2-{[6-(2,2-difluoro-3-phenylpropoxy)hexyl]amino}-1-hydroxyethyl)-2-(hydroxyl-methyl)phenol,
3-[2-(3-chloro-phenyl)-ethoxy]-N-(2-diethylamino-ethyl)-N-{2-[2-(4-hydroxy-2-oxo-2,3-dihydro-benzothiazole-7-yl)-ethylamino]-ethyl}-propionamide,
N-(2-diethylamino-ethyl)-N-{2-[2-(4-hydroxy-2-oxo-2,3-dihydro-benzothiazole-7-yl)-ethylamino]-ethyl}-3-(2-naphthalen-1-yl-ethoxy)-propionamide,
7-[2-(2-{3-[2-(2-chloro-phenyl)-ethylamino]-propylsulphanyl}-ethylamino)-1-hydroxy-ethyl]-4-hydroxy-3H-benzothiazol-2-one, optionally in the form of their racemates, enantiomers, diastereomers and optionally in the form of the pharmacologically acceptable acid addition salts, solvates or hydrates thereof. Preferably, according to the invention, the acid addition salts of the betamimetics are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Anticholinergics used according to the invention are preferably compounds selected from among the tiotropium salts, preferably the bromide salt, oxitropium salts, preferably the bromide salt, flutropium salts, preferably the bromide salt, Ipratropiumsalzen, preferably the bromide salt, aclidinium salts, preferably the bromide salt, glycopyrronium salts, preferably the bromide salt, trospium salts, preferably the chloride salt, tolterodine, (3R)-1-phenethyl-3-(9H-xanthene-9-carbonyloxy)-1-azoniabicyclo[2.2.2]octane salts. In the above-mentioned salts the cations are the pharmacologically active constituents. As anions $X^-$ the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while the chloride, bromide, iodide, sulphate, methanesulphonate or p-toluenesulphonate are preferred as counter-ions. Of all the salts the chlorides, bromides, iodides and methanesulphonates are particularly preferred.

Other anticholinergics may be selected from among
tropenol 2,2-diphenylpropionate-methobromide,
scopine 2,2-diphenylpropionate-methobromide,
scopine 2-fluoro-2,2-diphenylacetate methobromide,
tropenol 2-fluoro-2,2-diphenylacetate methobromide,
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide,
tropenol 9-hydroxy-fluorene-9-carboxylate methobromide,
tropenol 9-fluoro-fluorene-9-carboxylate methobromide,
scopine 9-hydroxy-fluorene-9-carboxylate methobromide,
scopine 9-fluoro-fluorene-9-carboxylate methobromide,
tropenol 9-methyl-fluorene-9-carboxylate methobromide,
scopine 9-methyl-fluorene-9-carboxylate methobromide,
cyclopropyltropine benzilate methobromide,
cyclopropyltropine 2,2-diphenylpropionate methobromide,
cyclopropyltropine 9-hydroxy-xanthene-9-carboxylate methobromide,
cyclopropyltropine 9-methyl-fluorene-9-carboxylate methobromide,
cyclopropyltropine 9-methyl-xanthene-9-carboxylate methobromide,
cyclopropyltropine 9-hydroxy-fluorene-9-carboxylate methobromide,
cyclopropyltropine methyl 4,4'-difluorobenzilate methobromide,
tropenol 9-hydroxy-xanthene-9-carboxylate methobromide,
scopine 9-hydroxy-xanthene-9-carboxylate methobromide,
tropenol 9-methyl-xanthene-9-carboxylate methobromide,
scopine 9-methyl-xanthene-9-carboxylate methobromide,
tropenol 9-ethyl-xanthene-9-carboxylate methobromide,
tropenol 9-difluoromethyl-xanthene-9-carboxylate methobromide, and
scopine 9-hydroxymethyl-xanthene-9-carboxylate methobromide.

Corticosteroids used according to the invention are preferably compounds selected from among beclomethasone betamethasone, budesonide, butixocort, ciclesonide, deflazacort, dexamethasone, etiprednol, flunisolide, fluticasone, loteprednol, mometasone, prednisolone, prednisone, rofleponide, triamcinolone and tipredane orpregna-1,4-diene-3,20-dione, 6-fluoro-11-hydroxy-16,17-[(1-methylethylidene)-bis(oxy)]-21-[[4-[(nitroxy)methyl]benzoyl]oxy], (6-alpha,11-beta,16-alpha)-(9CI) (NCX-1024)
16,17-butylidenedioxy-6,9-difluoro-11-hydroxy-17-(methylthio)androst-4-ene-3-one (RPR-106541),
(S)-fluoromethyl 6,9-difluoro-17-[(2-furanylcarbonyl)oxy]-11-hydroxy-16-methyl-3-oxo-androsta-1,4-diene-17-carbothionate,
(S)-(2-oxo-tetrahydrofuran-3S-yl) 6,9-difluoro-11-hydroxy-16-methyl-3-oxo-17-propionyloxy-androsta-1,4-diene-17-carbothionate, and
cyanomethyl 6-alpha,9-alpha-difluoro-11-beta-hydroxy-16alpha-methyl-3-oxo-17alpha-(2,2,3,3-tetramethylcyclopropylcarbonyl)oxy-androsta-1,4-diene-17beta-carboxylate,
optionally in the form of their racemates, enantiomers or diastereomers and optionally in the form of the salts and derivatives thereof, the solvates and/or hydrates thereof.

Every reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors used according to the invention are preferably compounds selected from among enprofyllin, theophyllin, roflumilast, ariflo (cilomilast), tofimilast, pumafentrin, lirimilast, apremilast, arofyllin, atizoram, oglemilast and tetomilast or
5-[(N-(2,5-dichloro-3-pyridinyl)-carboxamide]-8-methoxyquinoline (D-4418),
N-(3,5-dichloro-1-oxido-4-pyridinyl)-carboxamide]-8-methoxy-2-(trifluoromethyl)-quinoline (D-4396 (Sch-351591)), N-(3,5-dichloropyrid-4-yl)-[1-(4-fluorobenzyl)-5-hydroxy-indol-3-yl]glyoxylic acid amide (AWD-12-281 (GW-842470)), 9-[(2-fluorophenyl)methyl]-N-methyl-2-(trifluoromethyl)-9H-purin-6-amine (NCS-613),
4-[(2R)-2-[3-(cyclopentyloxy)-4-methoxyphenyl]-2-phenylethyl]-pyridine (CDP-840),
N-[(3R)-3,4,6,7-tetrahydro-9-methyl-4-oxo-1-phenylpyrrolo[3,2,1-jk][1,4]benzodiazepin-3-yl]-4-pyridinecarboxamide (PD-168787),
4-[6,7-diethoxy-2,3-bis(hydroxymethyl)-1-naphthalenyl]-1-(2-methoxyethyl)-2(1H)-pyridinone (T-440),
2-[4-[6,7-diethoxy-2,3-bis(hydroxymethyl)-1-naphthalenyl]-2-pyridinyl]-4-(3-pyridinyl)-1(2H)-phthalazinone (T-2585),
(3-(3-cyclopentyloxy-4-methoxybenzyl)-6-ethylamino-8-isopropyl-3H-purine (V-11294A),
beta-[3-(cyclopentyloxy)-4-methoxyphenyl]-1,3-dihydro-1,3-dioxo-2H-isoindole-2-propanamide (CDC-801),
imidazo[1,5-a]pyrido[3,2-e]pyrazin-6(5H)-one, 9-ethyl-2-methoxy-7-methyl-5-propyl-(D-22888)
5-[3-(cyclopentyloxy)-4-methoxyphenyl]-3-[(3-methylphenyl)methyl], (3S,5S)-2-piperidinone (HT-0712),
4-[1-[3,4-bis(difluoromethoxy)phenyl]-2-(3-methyl-1-oxido-4-pyridinyl)ethyl]-alpha,alpha-bis(trifluoromethyl)-benzenemethanol (L-826141),
N-(3,5-dichloro-1-oxo-pyridin-4-yl)-4-difluoromethoxy-3-cyclopropylmethoxybenzamide,
(−)p-[(4aR*,10bS*)-9-ethoxy-1,2,3,4,4a,10b-hexahydro-8-methoxy-2-methylbenzo[s]-[1,6]naphthyridin-6-yl]-N,N-diisopropylbenzamide,
(R)-(+)-1-(4-bromobenzyl)-4-[(3-cyclopentyloxy)-4-methoxyphenyl]-2-pyrrolidone,
3-(cyclopentyloxy-4-methoxyphenyl)-1-(4-N'-[N-2-cyano-5-methyl-isothioureido]-benzyl)-2-pyrrolidone,
cis[4-cyano-4-(3-cyclopentyloxy-4-methoxyphenyl)cyclohexane-1-carboxylic acid],
2-carbomethoxy-4-cyano-4-(3-cyclopropylmethoxy-4-difluoromethoxyphenyl)-cyclohexan-1-one,
cis[4-cyano-4-(3-cyclopropylmethoxy-4-difluoromethoxyphenyl)cyclohexan-1-ol],
(R)-(+)-ethyl[4-(3-cyclopentyloxy-4-methoxyphenyl)pyrrolidin-2-ylidene]acetate,
(S)-(−)-ethyl[4-(3-cyclopentyloxy-4-methoxyphenyl)pyrrolidin-2-ylidene]acetate,
9-cyclopentyl-5,6-dihydro-7-ethyl-3-(2-thienyl)-9H-pyrazolo[3,4-c]-1,2,4-triazolo-[4,3-a]pyridine and
9-cyclopentyl-5,6-dihydro-7-ethyl-3-(tert-butyl)-9H-pyrazolo[3,4-c]-1,2,4-triazolo-[4,3-a]pyridine,
optionally in the form of their racemates, enantiomers, diastereomers and optionally in the form of the pharmacologically acceptable acid addition salts, solvates or hydrates thereof. Preferably, according to the invention, acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTD4-receptor antagonists used according to the invention are preferably compounds selected from among montelukast, pranlukast and zafirlukast, or (E)-8-[2-[4-[4-(4-fluorophenyl)butoxy]phenyl]ethenyl]-2-(1H-tetrazol-5-yl)-4H-1-benzopyran-4-one (MEN-91507), 4-[6-acetyl-3-[3-(4-acetyl-3-hydroxy-2-propylphenylthio) propoxy]-2-propylphenoxy]-butyric acid (MN-001), 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid and

[2-[[2-(4-tert-butyl-2-thiazolyl)-5-benzofuranyl]oxymethyl]phenyl]acetic acid, optionally in the form of their racemates, enantiomers, diastereomers and optionally in the form of the pharmacologically acceptable acid addition salts, solvates or hydrates thereof. Preferably, according to the invention, acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-receptor antagonists may optionally be capable of forming are meant, for example: alkali metal salts, such as for example sodium or potassium salts, alkaline earth salts, sulphobenzoates, phosphates, isonicotinates, acetates, propionates, dihydrogen phosphates, palmitates, pivalates or furoates.

MAP Kinase inhibitors used according to the invention are preferably compounds selected from among:
Bentamapimod (AS-602801)
Doramapimod,
5-carbamoylindole (SD-169),
6-[(aminocarbonyl) (2,6-difluorophenyl)amino]-2-(2,4-difluorophenyl)-3-pyridinecarboxamide (VX-702),
alpha-[2-[[2-(3-pyridinyl)ethyl]amino]-4-pyrimidinyl]-2-benzothiazoleacetonitrile (AS-601245),
9,12-epoxy-1H-diindolo[1,2,3-fg:3'.2'.1'-kl]pyrrolo[3,4-i][1,6]benzodiazocine-10-carboxylic acid (CEP-1347), and
4-[3-(4-chlorophenyl)-5-(1-methyl-4-piperidinyl)-1H-pyrazol-4-yl]-pyrimidine (SC-409),
optionally in the form of their racemates, enantiomers, diastereomers and optionally in the form of the pharmacologically acceptable acid addition salts, prodrugs, solvates or hydrates thereof.

EGFR-inhibitors used according to the invention are preferably compounds selected from among cetuximab, trastuzumab, panitumumab (=ABX-EGF), Mab ICR-62, gefitinib, canertinib and erlotinib or 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-O-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxyethyl)-amino)-1-oxo-2-buten-1-yl]amino}-7-cyclopropylmethoxy-quinazoline, 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxyethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)-amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(R)tetrahydrofuran-2-yl)methoxy]-quinazoline,
4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline,
4-[(3-ethynyl-phenyl)amino]-6-{[4-(5.5-dimethyl-2-oxo-morpholin-4-yl)-1-oxo-2-buten-1-yl]amino}-quinazoline,
4-[(3-chloro-4-fluoro-phenyl)amino]-6-[2-(2,2-dimethyl-6-oxo-morpholin-4-yl)-ethoxy]-7-methoxy-quinazoline,
4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline,
4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline,
4-[(3-chloro-4-fluoro-phenyl)amino]-6-{2-[4-(2-oxo-morpholin-4-yl)-piperidin-1-yl]-ethoxy}-7-methoxy-quinazoline,
4-[(3-chloro-4-fluoro-phenyl)amino]-6-[1-(tert-butyloxycarbonyl)-piperidin-4-yloxy]-7-methoxy-quinazoline,
4-[(3-chloro-4-fluoro-phenyl)amino]-6-(trans-4-amino-cyclohexan-1-yloxy)-7-methoxy-quinazoline,
4-[(3-chloro-4-fluoro-phenyl)amino]-6-(trans-4-methanesulphonylamino-cyclohexan-1-yloxy)-7-methoxy-quinazoline,
4-[(3-chloro-4-fluoro-phenyl)amino]-6-(tetrahydropyran-3-yloxy)-7-methoxy-quinazoline,
4-[(3-chloro-4-fluoro-phenyl)amino]-6-(1-methyl-piperidin-4-yloxy)-7-methoxy-quinazoline,
4-[(3-chloro-4-fluoro-phenyl)amino]-6-{1-[(morpholin-4-yl)carbonyl]-piperidin-4-yloxy}-7-methoxy-quinazoline,
4-[(3-chloro-4-fluoro-phenyl)amino]-6-{1-[(methoxymethyl)carbonyl]-piperidin-4-yloxy}-7-methoxy-quinazoline,
4-[(3-chloro-4-fluoro-phenyl)amino]-6-(piperidin-3-yloxy)-7-methoxy-quinazoline,
4-[(3-chloro-4-fluoro-phenyl)amino]-6-[1-(2-acetylamino-ethyl)-piperidin-4-yloxy]-7-methoxy-quinazoline,
4-[(3-chloro-4-fluoro-phenyl)amino]-6-(tetrahydropyran-4-yloxy)-7-ethoxy-quinazoline,
4-[(3-chloro-4-fluoro-phenyl)amino]-6-((S)-tetrahydrofuran-3-yloxy)-7-hydroxy-quinazoline,
4-[(3-chloro-4-fluoro-phenyl)amino]-6-(tetrahydropyran-4-yloxy)-7-(2-methoxy-ethoxy)-quinazoline,
4-[(3-chloro-4-fluoro-phenyl)amino]-6-{trans-4-[(dimethylamino)sulphonylamino]-cyclohexan-1-yloxy}-7-methoxy-quinazoline,
4-[(3-chloro-4-fluoro-phenyl)amino]-6-{trans-4-[(morpholin-4-yl)carbonylamino]-cyclohexan-1-yloxy}-7-methoxy-quinazoline,
4-[(3-chloro-4-fluoro-phenyl)amino]-6-{trans-4-[(morpholin-4-yl)sulphonylamino]-cyclohexan-1-yloxy}-7-methoxy-quinazoline,
4-[(3-chloro-4-fluoro-phenyl)amino]-6-(tetrahydropyran-4-yloxy)-7-(2-acetylamino-ethoxy)-quinazoline,
4-[(3-chloro-4-fluoro-phenyl)amino]-6-(tetrahydropyran-4-yloxy)-7-(2-methanesulphonylamino-ethoxy)-quinazoline,
4-[(3-chloro-4-fluoro-phenyl)amino]-6-{1-[(piperidin-1-yl)carbonyl]-piperidin-4-yloxy}-7-methoxy-quinazoline,
4-[(3-chloro-4-fluoro-phenyl)amino]-6-(1-aminocarbonylmethyl-piperidin-4-yloxy)-7-methoxy-quinazoline,
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline,
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline,
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline,
4-[(3-chloro-4-fluoro-phenyl)amino]-6-(trans-4-ethanesulphonylamino-cyclohexan-1-yloxy)-7-methoxy-quinazoline,
4-[(3-chloro-4-fluoro-phenyl)amino]-6-(1-methanesulphonyl-piperidin-4-yloxy)-7-ethoxy-quinazoline,
4-[(3-chloro-4-fluoro-phenyl)amino]-6-(1-methanesulphonyl-piperidin-4-yloxy)-7-(2-methoxy-ethoxy)-quinazoline,
4-[(3-chloro-4-fluoro-phenyl)amino]-6-[1-(2-methoxy-acetyl)-piperidin-4-yloxy]-7-(2-methoxy-ethoxy)-quinazoline,
4-[(3-chloro-4-fluoro-phenyl)amino]-6-(cis-4-acetylamino-cyclohexan-1-yloxy)-7-methoxy-quinazoline,
4-[(3-ethynyl-phenyl)amino]-6-[1-(tert-butyloxycarbonyl)-piperidin-4-yloxy]-7-methoxy-quinazoline,
4-[(3-ethynyl-phenyl)amino]-6-(tetrahydropyran-4-yloxy]-7-methoxy-quinazoline,
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline,
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline,
4-[(3-chloro-4-fluoro-phenyl)amino]-6-{cis-4-[(morpholin-4-yl)carbonylamino-cyclohexan-1-yloxy}-7-methoxy-quinazoline,
4-[(3-chloro-4-fluoro-phenyl)amino]-6-{1-[2-(2-oxopyrrolidin-1-yl)ethyl]-piperidin-4-yloxy}-7-methoxy-quinazoline,
4-[(3-chloro-4-fluoro-phenyl)amino]-6-{1-[(morpholin-4-yl)carbonyl]-piperidin-4-yloxy}-7-(2-methoxy-ethoxy)-quinazoline,
4-[(3-ethynyl-phenyl)amino]-6-(1-acetyl-piperidin-4-yloxy)-7-methoxy-quinazoline,
4-[(3-ethynyl-phenyl)amino]-6-(1-methyl-piperidin-4-yloxy)-7-methoxy-quinazoline,
4-[(3-ethynyl-phenyl)amino]-6-(1-methanesulphonyl-piperidin-4-yloxy)-7-methoxy-quinazoline,
4-[(3-chloro-4-fluoro-phenyl)amino]-6-(1-methyl-piperidin-4-yloxy)-7(2-methoxy-ethoxy)-quinazoline,
4-[(3-chloro-4-fluoro-phenyl)amino]-6-(1-isopropyloxycarbonyl-piperidin-4-yloxy)-7-methoxy-quinazoline,
4-[(3-chloro-4-fluoro-phenyl)amino]-6-(cis-4-methylamino-cyclohexan-1-yloxy)-7-methoxy-quinazoline,
4-[(3-chloro-4-fluoro-phenyl)amino]-6-{cis-4-[N-(2-methoxy-acetyl)-N-methyl-amino]-cyclohexan-1-yloxy}-7-methoxy-quinazoline,
4-[(3-ethynyl-phenyl)amino]-6-(piperidin-4-yloxy)-7-methoxy-quinazoline,
4-[(3-ethynyl-phenyl)amino]-6-[1-(2-methoxy-acetyl)-piperidin-4-yloxy]-7-methoxy-quinazoline,
4-[(3-ethynyl-phenyl)amino]-6-{1-[(morpholin-4-yl)carbonyl]-piperidin-4-yloxy}-7-methoxy-quinazoline,
4-[(3-chloro-4-fluoro-phenyl)amino]-6-{1-[(cis-2,6-dimethyl-morpholin-4-yl)carbonyl]-piperidin-4-yloxy}-7-methoxy-quinazoline,
4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2.2.1]hept-5-yl)-carbonyl]-piperidin-4-yloxy}-7-methoxy-quinazoline,
4-[(3-chloro-4-fluoro-phenyl)amino]-6-{1-[(N-methyl-N-2-methoxyethyl-amino)carbonyl]-piperidin-4-yloxy}-7-methoxy-quinazoline,
4-[(3-chloro-4-fluoro-phenyl)amino]-6-(1-ethyl-piperidin-4-yloxy)-7-methoxy-quinazoline,
4-[(3-chloro-4-fluoro-phenyl)amino]-6-{1-[(2-methoxyethyl)carbonyl]-piperidin-4-yloxy}-7-methoxy-quinazoline,
4-[(3-chloro-4-fluoro-phenyl)amino]-6-{1-[(3-methoxypropyl-amino)-carbonyl]-piperidin-4-yloxy}-7-methoxy-quinazoline,
4-[(3-chloro-4-fluoro-phenyl)amino]-6-[cis-4-(N-methanesulphonyl-N-methyl-amino)-cyclohexan-1-yloxy]-7-methoxy-quinazoline,
4-[(3-chloro-4-fluoro-phenyl)amino]-6-[cis-4-(N-acetyl-N-methyl-amino)-cyclohexan-1-yloxy]-7-methoxy-quinazoline,
4-[(3-chloro-4-fluoro-phenyl)amino]-6-(trans-4-methylamino-cyclohexan-1-yloxy)-7-methoxy-quinazoline,
4-[(3-chloro-4-fluoro-phenyl)amino]-6-[trans-4-(N-methanesulphonyl-N-methyl-amino)-cyclohexan-1-yloxy]-7-methoxy-quinazoline,
4-[(3-chloro-4-fluoro-phenyl)amino]-6-(trans-4-dimethylamino-cyclohexan-1-yloxy)-7-methoxy-quinazoline,
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline,
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline,
4-[(3-chloro-4-fluoro-phenyl)amino]-6-(1-methanesulphonyl-piperidin-4-yloxy)-7-methoxy-quinazoline,
4-[(3-chloro-4-fluoro-phenyl)amino]-6-(1-cyano-piperidin-4-yloxy)-7-methoxy-quinazoline,
3-cyano-4-[(3-chloro-4-fluorophenyl)amino]-6-{[4-(N,N-dimethylamino)-1-oxo-2-buten-1-yl]amino}-7-ethoxy-quinoline;
[4-[(3-chloro-4-fluorophenyl)amino]-6-{[4-(homomorpholin-4-yl)-1-oxo-2-buten-1-yl]-amino}-7-[(S)-(tetrahydrofuran-3-yl)oxy]-quinazoline,
4-[(3-chloro-4-fluorophenyl)amino]-7-(2-{4-[(S)-(2-oxotetrahydrofuran-5-yl)carbonyl]-piperazin-1-yl}-ethoxy)-6-[(vinylcarbonyl)amino]-quinazoline,
4-[(3-chloro-4-fluorophenyl)amino]-7-[2-((S)-6-methyl-2-oxo-morpholin-4-yl)-ethoxy]-6-[(vinylcarbonyl)amino]-quinazoline,
4-[(3-chloro-4-fluorophenyl)amino]-7-[4-((R)-6-methyl-2-oxo-morpholin-4-yl)-butyloxy]-6-[(vinylcarbonyl)amino]-quinazoline,
4-[(3-chloro-4-fluorophenyl)amino]-7-[4-((S)-6-methyl-2-oxo-morpholin-4-yl)-butyloxy]-6-[(vinylcarbonyl)amino]-quinazoline, and
4-[(3-chloro-4-fluorophenyl)amino]-6-[(4-{N-[2-(ethoxycarbonyl)-ethyl]-N-[(ethoxy-carbonyl)methyl]amino}-1-oxo-2-buten-1-yl)amino]-7-cyclopropylmethoxy-quinazoline,
optionally in the form of their racemates, enantiomers or diastereomers, optionally in the form of the pharmacologically acceptable acid addition salts, solvates and/or hydrates thereof. Preferably, according to the invention, acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Histamine H1 receptor antagonists used according to the invention are preferably compounds selected from among epinastin, cetirizin, azelastin, fexofenadin, levocabastin, loratadine, mizolastin, ketotifen, emedastine, dimetindene, clemastine, bamipine, cexchlorpheniramine, pheniramine, doxylamine, chlorophenoxamine, dimenhydrinate, diphenhydramine, promethazine, ebastine, olopatadine, desloratidine and meclozine, optionally in the form of their racemates, enantiomers, diastereomers and optionally in the form of the pharmacologically acceptable acid addition salts, solvates or hydrates thereof. Preferably, according to the invention, the acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Histamine H4 receptor antagonists used according to the invention are preferably compounds such as for example (5-chloro-1H-indol-2-yl)-(4-methyl-1-piperazinyl)-methanone (JNJ-7777120), optionally in the form of their racemates, enantiomers, diastereomers and optionally in the form of the pharmacologically acceptable acid addition salts, solvates or hydrates thereof. Preferably, according to the invention, acid addition salts selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate are used.

PAF-antagonists used according to the invention are preferably compounds selected from among lexipafant and the compounds
4-(2-chlorophenyl)-9-methyl-2-[3(4-morpholinyl)-3-propanon-1-yl]-6H-thieno-[3,2-f]-[1,2,4]triazolo[4,3-a][1,4]diazepine and
6-(2-chlorophenyl)-8,9-dihydro-1-methyl-8-[(4-morpholinyl)carbonyl]-4H,7H-cyclo-penta-[4,5]thieno[3,2-f][1,2,4]triazolo[4,3-a][1,4]diazepine,
optionally in the form of their racemates, enantiomers, diastereomers and optionally in the form of the pharmacologically acceptable acid addition salts, solvates or hydrates thereof. Preferably, according to the invention, the acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

PI3-Kinase inhibitors used according to the invention are preferably compounds selected from among
5-(quinoxalin-6-ylmethylene)thiazolidine-2,4-dione (AS-605240),
2-[(6-amino-9H-purin-9-yl)methyl]-5-methyl-3-(2-methylphenyl)-4(3H)-quinazolinone (C-87114) and
2-methyl-2-[4-[3-methyl-2-oxo-8-(quinoline-3-yl)-2,3-dihydroimidazo[4,5-c]quinolin-1-yl]phenyl]propionitrile (BEZ-235),
optionally in the form of the racemates, enantiomers, diastereomers thereof and optionally in the form of the pharmacologically acceptable acid addition salts, prodrugs, solvates or hydrates thereof.

CXCR1 or CXCR2 antagonists used according to the invention are preferably compounds selected from among 3-[[3-[(dimethylamino)carbonyl]-2-hydroxyphenyl]amino]-4-[[(R)-1-(5-methylfuran-2-yl)propyl]amino]cyclobut-3-ene-1,2-dione (SCH-527123), optionally in the form of the racemates, enantiomers, diastereomers thereof and optionally in the form of the pharmacologically acceptable acid addition salts, prodrugs, solvates or hydrates thereof.

Antitussive substances used according to the invention are preferably compounds selected from among hydrocodone, caramiphen, carbetapentane and dextramethorphane, optionally in the form of their racemates, enantiomers, diastereomers and optionally in the form of the pharmacologically acceptable acid addition salts, prodrugs, solvates or hydrates thereof.

For treating inflammatory and/or oedematous diseases of the skin and mucous membranes the compounds of general formula I according to the invention may be combined for example with substances selected from among methotrexate, cyclosporin, topical steroids, topical calcineurin inhibitors, vitamin D analogues, fumarates, PDE4-inhibitors and TNF-antagonists, optionally in the form of their racemates, enantiomers, diastereomers and optionally in the form of the pharmacologically acceptable acid addition salts, prodrugs, solvates or hydrates thereof.

Calcineurin inhibitors used according to the invention are preferably compounds selected from among tacrolimus and pimecrolimus.

A vitamin D analogue preferably used according to the invention is calcipotriol.

A fumurate preferably used according to the invention is BG 12 (oral fumurate).

TNF-antagonists used according to the invention are preferably compounds selected from among etanercept (Enbrel), infliximab (Remicade) and adalimumab (Humira).

The dosage necessary for obtaining a pain-alleviating effect is, in the case of intravenous administration, expediently from 0.01 to 3 mg/kg of body weight, preferably from 0.1 to 1 mg/kg, and, in the case of oral administration, from 0.1 to 8 mg/kg of body weight, preferably from 0.5 to 3 mg/kg, in each case once, twice or three times per day. The compounds prepared according to the invention can be administered intravenously, subcutaneously, intramuscularly, intrarectally, intranasally, by inhalation, transdermally or orally, aerosol formulations being particularly suitable for inhalation. They can be incorporated into customary pharmaceutical preparations, such as tablets, coated tablets, capsules, powders, suspensions, solutions, metered-dose aerosols or suppositories, if appropriate together with one or more customary inert carriers and/or diluents, for example with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances, such as hardened fat, or suitable mixtures thereof.

EXPERIMENTAL SECTION

Generally, there are mass spectra and/or $^1$H NMR spectra for the compounds that have been prepared. The ratios given for the eluants are in volume units of the solvents in question. For ammonia, the given volume units are based on a concentrated solution of ammonia in water. Unless indicated otherwise, the acid, base and salt solutions used for working up the reaction solutions are aqueous systems having the stated concentrations.

For chromatographic purification, silica gel from Millipore (MATREX™, 35 to 70 μm) or Alox (E. Merck, Darmstadt, Alumina 90 standardized, 63 to 200 μm, article No. 1.01097.9050) is used.

In the descriptions of the experiments, the following abbreviations are used:

| | |
|---|---|
| TLC | thin layer chromatograph |
| DIPEA | diisopropylethylamine |
| DMA | N,N-dimethylacetamide |
| DMAP | 4-dimethylaminopyridine |
| DMF | N,N-dimethylformamide |
| DMSO | dimethylsulphoxide |
| HATU | O-(7-azabenzotriazol-1-yl)-N,N,N',N'-tetramethyluronium hexafluorophosphate |
| $Pd_2(dba)_3$ | tris(dibenzylideneacetone)-dipalladium(0) |
| RP | reverse phase |
| $R_t$ | retention time |
| tert | tertiary |
| TBTU | 2-(1H-benzotriazol-1-yl)-1,1,3,3-tetramethyluronium-tetrafluoroborate |
| TEA | triethylamine |
| THF | tetrahydrofuran |
| XPhos | 2-dicyclohexyl-phosphino-2',4',6'-tri-isopropyl-1,1'-biphenyl |

The following analytical HPLC methods were used:

| Method 1: | Column: | Merck Cromolith Flash RP18e, 4.6 × 25 mm |
|---|---|---|
| | Eluant A: | water/0.1% formic acid |
| | Eluant B: | acetonitrile/0.1% formic acid |

| Gradient: | | | |
|---|---|---|---|
| time in min | % A | % B | flow rate in mL/min |
| 0.0 | 90.0 | 10.0 | 1.6 |
| 2.7 | 10.0 | 90.0 | 1.6 |
| 3.0 | 10.0 | 90.0 | 1.6 |
| 3.3 | 90.0 | 10.0 | 1.6 |

| Method 2: | Column: | Waters, Sunfire C18, 4.6 × 30 mm; 3.5 μm |
|---|---|---|
| | Eluant A: | water/0.1% trifluoroacetic acid |
| | Eluant B: | methanol/0.1% trifluoroacetic acid |
| | Temperature: | 60° C. |

| Gradient: | | | |
|---|---|---|---|
| time in min | % A | % B | flow rate in mL/min |
| 0.0 | 95 | 5 | 4.0 |
| 0.15 | 95 | 5 | 4.0 |
| 1.7 | 0 | 100 | 4.0 |
| 2.25 | 0 | 100 | 4.0 |

| Method 3: | Column: | Waters, Xbridge, C18, 4.6 × 30 mm; 3.5 μm |
|---|---|---|
| | Eluant A: | water/0.1% trifluoroacetic acid |
| | Eluant B: | methanol/0.1% trifluoroacetic acid |
| | Temperature: | 60° C. |

| Gradient: | | | |
|---|---|---|---|
| time in min | % A | % B | flow rate in mL/min |
| 0.0 | 95 | 5 | 4.0 |
| 0.15 | 95 | 5 | 4.0 |
| 1.7 | 0 | 100 | 4.0 |
| 2.25 | 0 | 100 | 4.0 |

| Method 4: | Column: | Agilent, StableBond, C18, 3 × 30 mm; 1.8 μm |
|---|---|---|
| | Eluant A: | water/0.1% trifluoroacetic acid |
| | Eluant B: | acetonitrile |
| | Temperature: | 60° C. |

| Gradient: | | | |
|---|---|---|---|
| time in min | % A | % B | flow rate in mL/min |
| 0.0 | 95 | 5 | 2.2 |
| 0.05 | 95 | 5 | 2.2 |
| 1.40 | 0 | 100 | 2.2 |
| 1.80 | 0 | 100 | 2.2 |

Preparation of the End Compounds

Example 1

(S)-6-oxo-1,6-dihydro-pyridazine-4-carboxylic acid-{3-[2-fluoro-4-(4-methoxy-2-trifluoromethyl-phenylamino)-benzylcarbamoyl]-tetrahydrofuran-3-yl}-amide

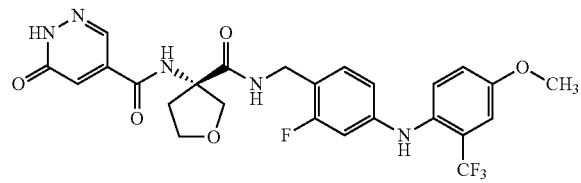 [SMILES: COc1ccc(Nc2ccc(CNC(=O)[C@]3(NC(=O)c4cn[nH]c(=O)c4)CCOC3)c(F)c2)c(C(F)(F)F)c1]

1a) 2-fluoro-4-(4-methoxy-2-trifluoromethyl-phenylamino)-benzonitrile

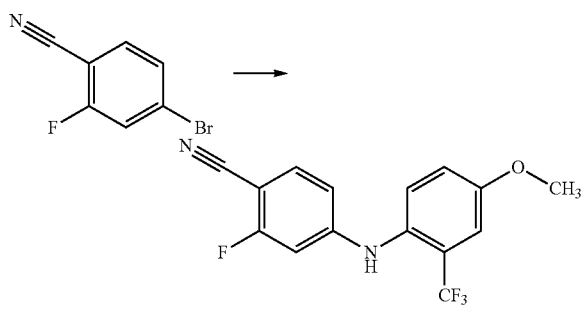

2-Amino-5-methoxy-benzotrifluoride (10.46 mmol), $K_3PO_4$ (15.7 mmol), Xphos (1.05 mmol) and $Pd_4(dba)_3$ (0.314 mmol) were added under nitrogen to a solution of 4-bromo-2-fluoro-benzonitrile (10.46 mmol) in 50 mL toluene and the mixture was stirred for 20 hours at a bath temperature of 110° C. Then the mixture was filtered through a glass fibre filter, then the filtrate was extracted with 150 mL water. The organic phase was dried on sodium sulphate and evaporated down. In this way the product was obtained in a yield of 87% of theory.

$C_{15}H_{10}F_4N_2O$ (310.2)
Mass spectrum (ESI): [M+H]+=311
[M−H]−=309
Thin layer chromatograph (silica gel; petroleum ether/ethyl acetate 7:3): $R_f$=0.48

1b) 2-fluoro-4-(4-methoxy-2-trifluoromethyl-phenylamino)-benzylamine

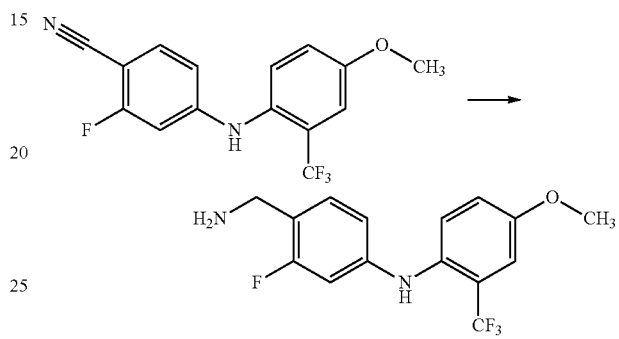

2-fluoro-4-(4-methoxy-2-trifluoromethyl-phenylamino)-benzonitrile (2.85 g, 9.19 mmol) was hydrogenated in 40 mL saturated methanolic ammonia solution after the addition of 300 mg of Raney nickel at ambient temperature. After the catalyst had been filtered off and the mixture evaporated down the product was obtained in a yield of 99% of theory.

$C_{15}H_{14}F_4N_2O$ (314.3)
Thin layer chromatograph (silica gel; dichloromethane/ethanol 19:1): $R_f$=0.21

1c) n-butyl(S)-3-[(6-oxo-1,6-dihydro-pyridazine-4-carbonyl)-amino]-tetrahydrofuran-3-carboxylate

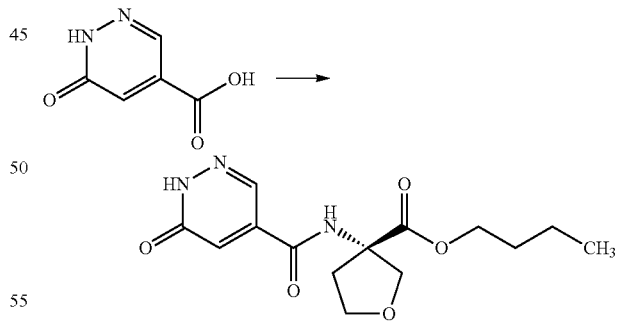

A solution of 6-oxo-1,6-dihydro-pyridazine-4-carboxylic acid (10.5 g, 74.9 mmol), TBTU (25.3 g, 78.7 mmol), triethylamine (20.9 mL) and 40 mL DMF in 200 mL THF was stirred for 30 minutes at ambient temperature. Then n-butyl(S)-3-amino-tetrahydrofuran-3-carboxylate (14.0 g, 74.9 mmol) was added and the mixture was stirred further overnight. For working up the mixture was evaporated to dryness in vacuo and the residue was stirred with 200 mL ethyl acetate. This solution was washed twice with 5% sodium hydrogen carbonate solution, then dried and evaporated down.

The product was thus obtained in a yield of 90% of theory.
C$_{14}$H$_{19}$N$_3$O$_5$ (309.3)

Thin layer chromatograph (silica gel; dichloromethane/ethanol 19:1): R$_f$=0.16

1d) (S)-3-[(6-oxo-1,6-dihydro-pyridazine-4-carbonyl)-amino]-tetrahydro-furan-3-carboxylic acid

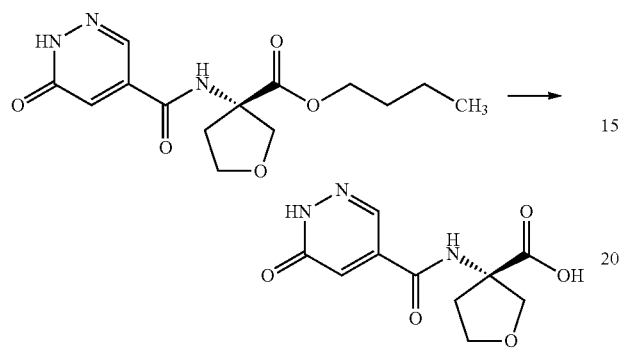

n-Butyl(S)-3-[(6-oxo-1,6-dihydro-pyridazine-4-carbonyl)-amino]-tetrahydrofuran-3-carboxylate (21.0 g, 67.9 mmol) was stirred vigorously in 200 mL of 1N sodium hydroxide solution for 1 hour. The mixture was then extracted twice with 100 mL of diethyl ether, the alkaline aqueous phase was then combined with 50 mL of 4N hydrochloric acid. The mixture was then evaporated to dryness and the residue was stirred with 150 mL ethanol. Undissolved ingredients were then filtered off and the filtrate was evaporated down. In this way the product was obtained in a yield of 71% of theory. The product thus obtained was further processed without purification.
C$_{10}$H$_{11}$N$_3$O$_5$ (253.2)
$^1$H-NMR (d$_6$-DMSO): δ=2.32 (m, 2H); 3.84 (t, 2H); 3.95 (d, 1H); 4.12 (d, 1H); 7.28 (s, 1H); 8.10 (s, 1H); 9.21 (broad S; 1H).

1e) (S)-6-oxo-1,6-dihydro-pyridazine-4-carboxylic acid-{3-[2-fluoro-4-(4-methoxy-2-tri-fluoromethyl-phenylamino)-benzylcarbamoyl]-tetrahydrofuran-3-yl}-amide

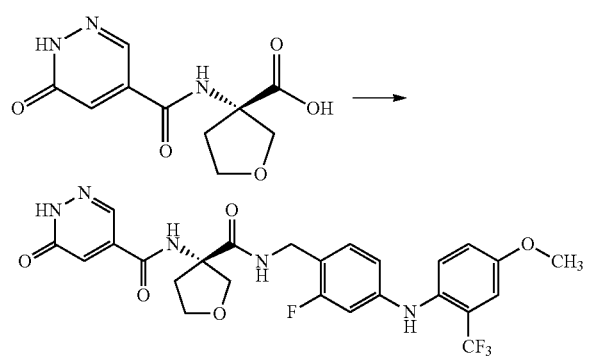

(S)-3-[(6-oxo-1,6-dihydro-pyridazine-4-carbonyl)-amino]-tetrahydrofuran-3-carboxylic acid (0.55 mmol) was dissolved in a mixture of 30 mL tetrahydrofuran, 4 mL DMF and 0.15 mL triethylamine, then TBTU (0.19 g, 0.58 mmol) was added and the mixture was stirred for 30 minutes at ambient temperature. Then 2-fluoro-4-(4-methoxy-2-trifluoromethyl-phenylamino)-benzylamine (0.17 g, 0.55 mMol, from 1b) was added and the mixture was stirred for a further two hours. As there was still some unreacted amine present, another 10 mg of the acid and 20 mg TBTU were added and the mixture was stirred further overnight. Then the solvents were evaporated off and the residue was chromatographed on silica gel (eluant: dichloromethane/methanol/ammonia: 95/5/0.5). In this way the product was obtained in a yield of 19% of theory.

C$_{25}$H$_{23}$F$_4$N$_5$O$_5$ (549.5)

Mass spectrum (ESI): [M+H]+=550

[M-H]-=548

Thin layer chromatograph (silica gel; dichloromethane/methanol/ammonia: 9/1/0.1): R$_f$=0.46

Example 2

(S)-5-amino-N-{3-[2-fluoro-4-(4-methoxy-2-trifluoromethyl-phenylamino)-benzylcarbamoyl]-tetrahydro-furan-3-yl}-nicotinamide

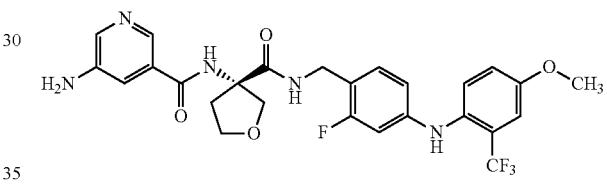

2a) n-Butyl(S)-3-[(5-amino-pyridine-3-carbonyl)-amino]-tetrahydrofuran-3-carboxylate

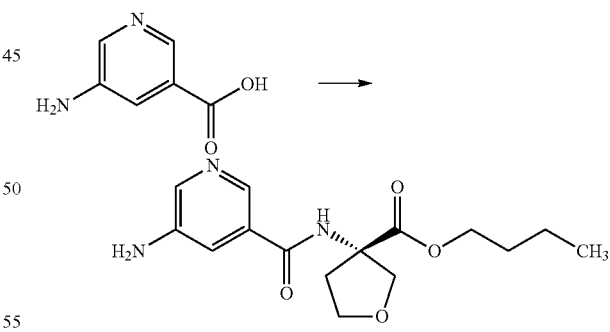

Analogously to Example 1c), 5-aminopyridine-3-carboxylic acid (72.4 mmol) was reacted with n-butyl(S)-3-amino-tetrahydrofuran-3-carboxylate (72.4 mmol). The product was obtained in a yield of 96% of theory.

C$_{15}$H$_{21}$N$_3$O$_4$ (307.3)

Mass spectrum (ESI): [M+H]+=308

[M-H]-=306

Thin layer chromatograph (silica gel; ethyl acetate/ethanol 9:1): R$_f$=0.58

2b) (S)-3-[(5-amino-pyridine-3-carbonyl)-amino]-tetrahydrofuran-3-carboxylic acid

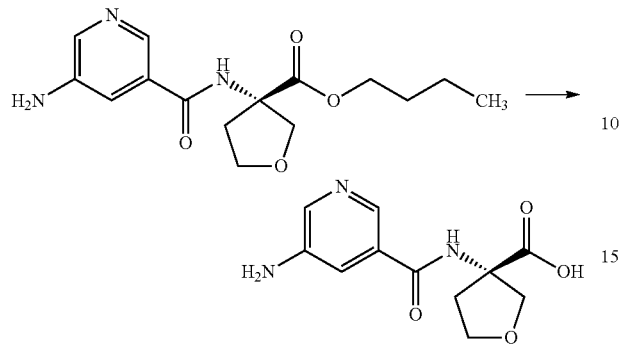

Analogously to Example 1d), n-butyl(S)-3-[(5-amino-pyridine-3-carbonyl)-amino]-tetrahydrofuran-3-carboxylate (69.9 mmol) was saponified with sodium hydroxide solution.

The product was obtained in a yield of 86% of theory.

$C_{11}H_{13}N_3O_4$ (251.2)

Mass spectrum (ESI): [M+H]+=252

$^1$H-NMR (d$_6$-DMSO): δ=2.33 (m, 2H); 3.82 (m, 2H); 5.48 (broad s, 2H); 7.27 (s, 1H); 8.03 (s, 1H); 8.18 (s, 1H); 8.85 (s, 1H); 12.60 (broad s, 1H) ppm.

2c) (S)-5-amino-N-{3-[2-fluoro-4-(4-methoxy-2-trifluoromethyl-phenylamino)-benzyl-carbamoyl]-tetrahydro-furan-3-yl}-nicotinamide

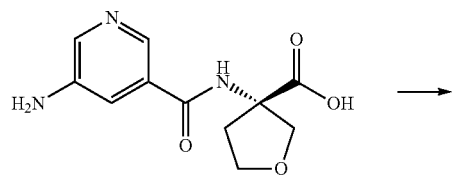

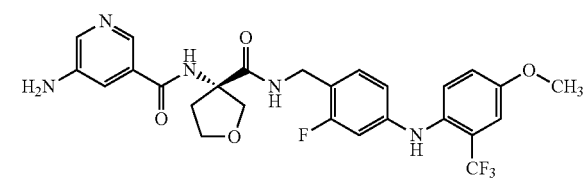 [SMILES: COc1ccc(Nc2ccc(CNC(=O)[C@]3(NC(=O)c4cncc(N)c4)CCOC3)c(F)c2)c(C(F)(F)F)c1]

Analogously to Example 1e), (S)-3-[(5-amino-pyridine-3-carbonyl)-amino]-tetrahydrofuran-3-carboxylic acid (0.55 mmol) was reacted with 2-fluoro-4-(4-methoxy-2-trifluoromethyl-phenylamino)-benzylamine (0.55 mMol, from 1b). The product was obtained in a yield of 27% of theory.

$C_{26}H_{25}F_4N_5O_4$ (547.5)

Mass spectrum (ESI): [M+H]+=548

[M−H]=−546

HPLC: $R_t$=2.44 min (method 1)

Example 3

(S)-5-amino-N-(3-{[3-fluoro-5-(4-methoxy-2-trifluoromethyl-phenylamino)-pyridin-2-ylmethyl]-carbamoyl}-tetrahydrofuran-3-yl)-nicotinamide

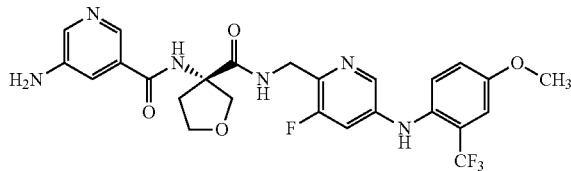 [SMILES: COc1ccc(Nc2cnc(CNC(=O)[C@]3(NC(=O)c4cncc(N)c4)CCOC3)c(F)c2)c(C(F)(F)F)c1]

3a) tert-butyl (5-bromo-3-fluoro-pyridin-2-ylmethyl)-carbamate

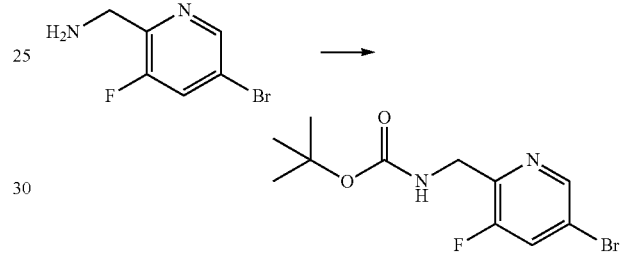

A solution of 2-aminomethyl-3-fluoro-5-bromopyridine (185 mg, 0.77 mmol) in 8 mL dichloromethane was combined with 0.32 mL triethylamine and di-tert-butyl-dicarbonate (167.2 mg, 0.77 mmol) while cooling with an ice bath and then stirred overnight at ambient temperature. After standard working up of the reaction mixture the product was obtained in a yield of 72% of theory.

$C_{11}H_{14}BrFN_2O_2$ (305.14)

MS (ESI): [M+H]+=305/7

HPLC: $R_t$=2.31 min (method 1)

3b) tert-butyl[3-fluoro-5-(4-methoxy-2-trifluoromethyl-phenylamino)-pyridin-2-ylmethyl]-carbamate

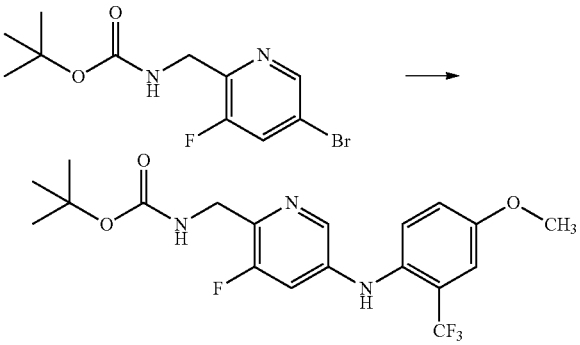

Analogously to Example 1a), tert-butyl (5-bromo-3-fluoro-pyridin-2-ylmethyl)-carbamate (0.55 mmol) was reacted with 4-methoxy-2-trifluoromethyl-aniline. The crude product was purified by chromatography (column: Varian Pursuit XRS C18; 10 μM; 41.4×250 mm, gradient: acetonitrile/water/CF₃COOH: 10/90/0.1→100/0/0.1). The product was thus obtained in a yield of 26% of theory.

$C_{19}H_{21}F_4N_3O_3$ (415.4)
MS (ESI): [M+H]+=416
HPLC: $R_t$=2.77 min (method 1)

3c) (6-aminomethyl-5-fluoro-pyridin-3-yl)-(4-methoxy-2-trifluoromethyl-phenyl)-amine

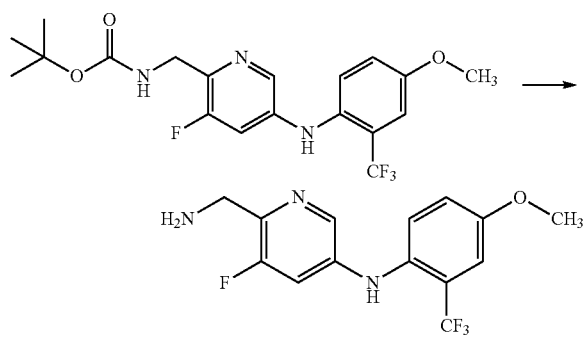

Tert-butyl[3-fluoro-5-(4-methoxy-2-trifluoromethyl-phenylamino)-pyridin-2-ylmethyl]-carbamate (0.13 mmol) was stirred for two hours at 60° C. in a mixture of 2 mL semi-concentrated hydrochloric acid and 3 mL dioxane. The mixture was then evaporated to dryness, then the residue was stirred with 3 mL toluene and evaporated down again. The crude product thus obtained (89% of theory) was used further without purification.

$C_{14}H_{13}F_4N_3O$ (315.3)
MS (ESI): [M+H]+=316

3d) (S)-5-amino-N-(3-{[3-fluoro-5-(4-methoxy-2-trifluoromethyl-phenylamino)-pyridin-2-ylmethyl]-carbamoyl}-tetrahydro-furan-3-yl)-nicotinamide

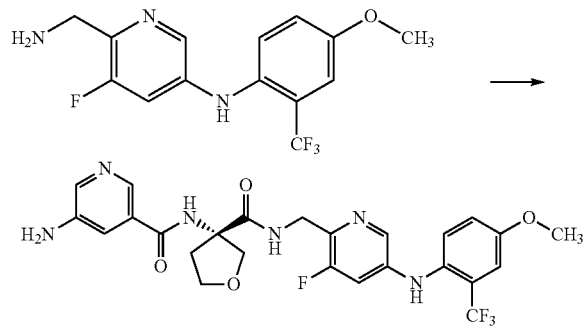

Analogously to Example 1e), (S)-3-[(5-amino-pyridine-3-carbonyl)-amino]-tetrahydrofuran-3-carboxylic acid (from 2b) was reacted with (6-aminomethyl-5-fluoro-pyridin-3-yl)-(4-methoxy-2-trifluoromethyl-phenyl)-amine. The product was obtained in a yield of 34% of theory.

$C_{25}H_{24}F_4N_6O_4$ (548.5)
MS (ESI): [M+H]+=549
HPLC: $R_t$=2.55 min (method 1)

Example 4

(S)-5-amino-N-{3-[4-(4-methoxy-2-trifluoromethyl-phenylamino)-benzylcarbamoyl]-tetrahydrofuran-3-yl}-nicotinamide

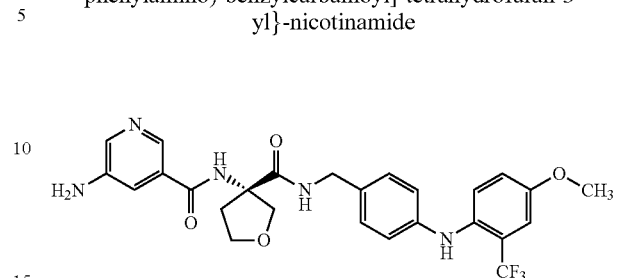

4a) 4-(4-methoxy-2-trifluoromethyl-phenylamino)-benzonitrile

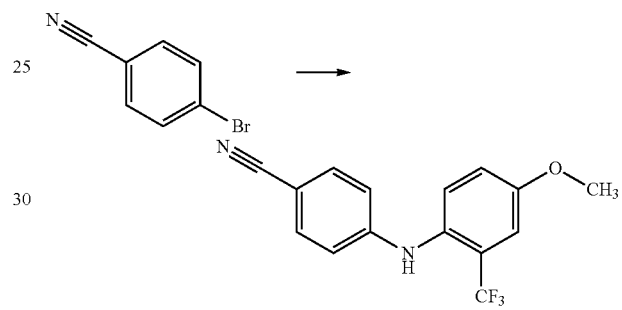

Analogously to Example 1a), 4-bromobenzonitrile was reacted with 2-trifluoromethyl-4-methoxy-aniline. After chromatographic purification through silica gel (petroleum ether with 10 to 30% ethyl acetate) the 4-(4-methoxy-2-trifluoromethyl-phenylamino)-benzonitrile was obtained in a yield of 60.5% of theory.

$C_{15}H_{11}F_3N_2O$ (292.3)
Mass spectrum (ESI): [M+H]⁺=293
[M−H]⁻=291

4b) (4-aminomethyl-phenyl)-(4-methoxy-2-trifluoromethyl-phenyl)-amine

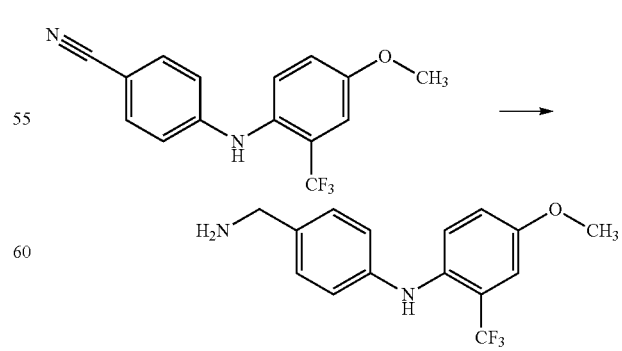

3.7 g (12.7 mmol) of 4-(4-methoxy-2-trifluoromethyl-phenylamino)-benzonitrile were hydrogenated in a 7N solution of ammonia in methanol (100 mL) with the addition of Raney nickel at ambient temperature. After the catalyst had been filtered off and the solvent distilled off, the crude product thus obtained was reacted further without purification.

$C_{15}H_{15}F_3N_2O$ (296.3)

4c) (S)-5-amino-N-{3-[4-(4-methoxy-2-trifluoromethyl-phenylamino)-benzylcarbamoyl]-tetrahydrofuran-3-yl}-nicotinamide

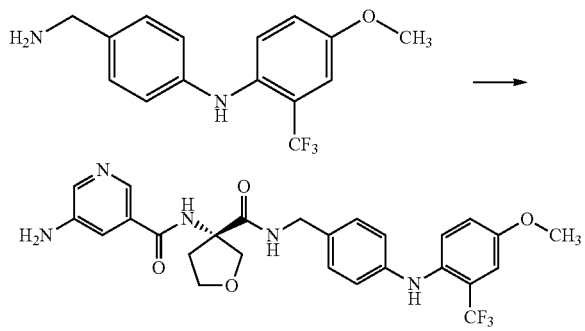

Analogously to Example 1e), (S)-3-[(5-amino-pyridine-3-carbonyl)-amino]-tetrahydrofuran-3-carboxylic acid (1.00 mmol) was reacted with (4-aminomethyl-phenyl)-(4-methoxy-2-trifluoromethyl-phenyl)-amine (1.00 mMol, from Example 4b)). The product was obtained in a yield of 32% of theory.

$C_{26}H_{26}F_3N_5O_4$ (529.5)
Mass spectrum (ESI): [M+H]+=530
[M–H]–=528
HPLC: $R_f$=0.842 min (method 4)
Thin layer chromatograph (silica gel; dichloromethane/ethanol 9:1+1% NH$_4$OH): $R_f$=0.25

Example 5

(S)-5-amino-N-(3-{[5-(4-methoxy-2-trifluoromethyl-phenylamino)-pyridin-2-ylmethyl]-carbamoyl}-tetrahydrofuran-3-yl)-nicotinamide

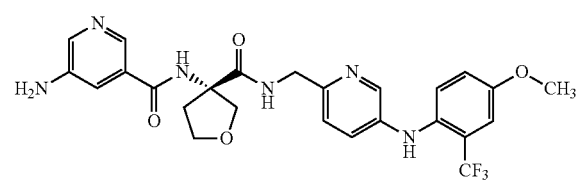 [SMILES: COc1ccc(Nc2ccc(CNC(=O)[C@]3(NC(=O)c4cncc(N)c4)CCOC3)nc2)c(C(F)(F)F)c1]

5a) 5-(4-methoxy-2-trifluoromethyl-phenylamino)-pyridine-2-carbonitrile

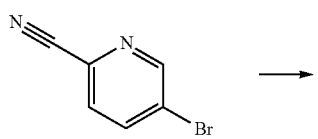

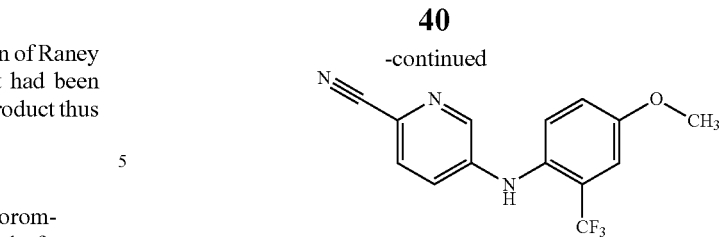

Analogously to Example 1a) 5-bromo-pyridine-2-carbonitrile was reacted with 2-trifluoromethyl-4-methoxy-aniline. After chromatographic purification through silica gel (petroleum ether with 10 to 30% ethyl acetate) the 4-(4-methoxy-2-trifluoromethyl-phenyl-amino)-benzonitrile was obtained in a yield of 97.4% of theory.

$C_{14}H_{10}F_3N_3O$ (293.2)
Mass spectrum (ESI): [M+H]+=294
[M–H]–=292
$^1$H-NMR (d$_6$-DMSO): δ=3.87 (s, 3H); 6.88 (dd, 1H); 7.31 (m, 2H); 7.47 (d, 1H); (7.67 (d, 1H); 8.11 (s, 1H); 8.62 (s, 1H) ppm.

5b) (6-aminomethyl-pyridin-3-yl)-(4-methoxy-2-trifluoromethyl-phenyl)-amine

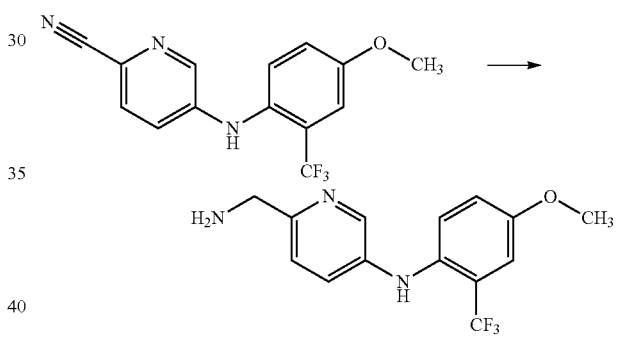

Analogously to Example 4b, 5-(4-methoxy-2-trifluoromethyl-phenylamino)-pyridine-2-carbonitrile (1.71 mmol) was hydrogenated in a 7N solution of ammonia in methanol (30 mL) with the addition of Raney nickel at ambient temperature. After the catalyst had been filtered off and the solvent distilled off, the crude product thus obtained was further reacted without purification.

$C_{14}H_{14}F_3N_3O$ (297.3)
Thin layer chromatograph (silica gel; dichloromethane/ethanol 9:1): $R_f$=0.11

5c) n-butyl(S)-3-[(5-tert-butoxycarbonylamino-pyridine-3-carbonyl)-amino]-tetrahydrofuran-3-carboxylate

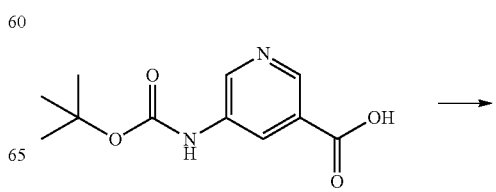

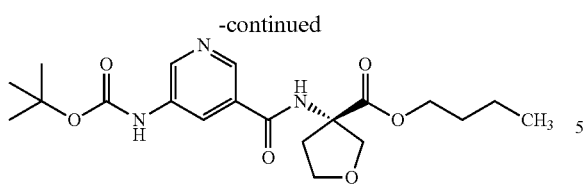

A suspension of 5-tert-butoxycarbonylamino-pyridine-3-carboxylic acid (2.5 mmol) in 20 mL tetrahydrofuran was combined with N,N-carbodiimidazole (2.75 mmol) and stirred for 15 minutes at ambient temperature. Then a solution of n-butyl(S)-3-amino-tetrahydrofuran-3-carboxylate (2.5 mmol) in 4 mL tetrahydrofuran was added and the reaction mixture was stirred further overnight. Then the solvent was distilled off and the crude product thus obtained was purified by chromatography (silica gel; dichloromethane with 1-25% ethanol).

Yield: 31% of theory
$C_{20}H_{29}N_3O_6$ (407.5)
Mass spectrum (ESI): [M+H]$^+$=408
[M−H]$^-$=406

5d) (S)-3-[(5-tert-butoxycarbonylamino-pyridin-3-carbonyl)-amino]-tetrahydrofuran-3-carboxylic acid

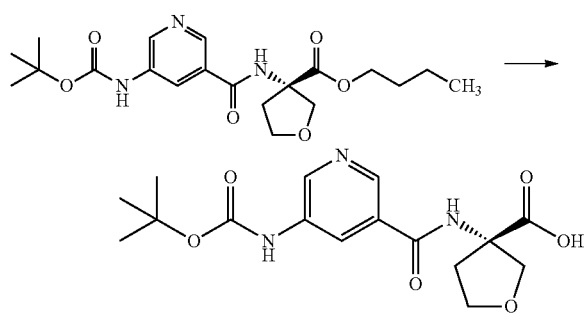

A solution of n-butyl(S)-3-[(5-tert-butoxycarbonylamino-pyridin-3-carbonyl)-amino]-tetra-hydrofuran-3-carboxylate (29.7 mmol) in 150 mL methanol was combined with 60 mL of 1N sodium hydroxide solution and stirred for three hours at ambient temperature. Then the methanol was distilled off, the solution was then washed with 50 mL tert-butylmethylether and then adjusted to pH 3 with 4N hydrochloric acid. The product that then precipitated was filtered off and further reacted without purification.

Yield: 94% of theory
$C_{16}H_{21}N_3O_6$ (351.4)
Mass spectrum (ESI): [M+H]$^+$=352
[M−H]$^-$=350

5e) tert-butyl(S)-[5-(3-{[5-(4-methoxy-2-trifluoromethyl-phenylamino)-pyridin-2-ylmethyl]-carbamoyl}-tetrahydrofuran-3-ylcarbamoyl)-pyridin-3-yl]-carbamate

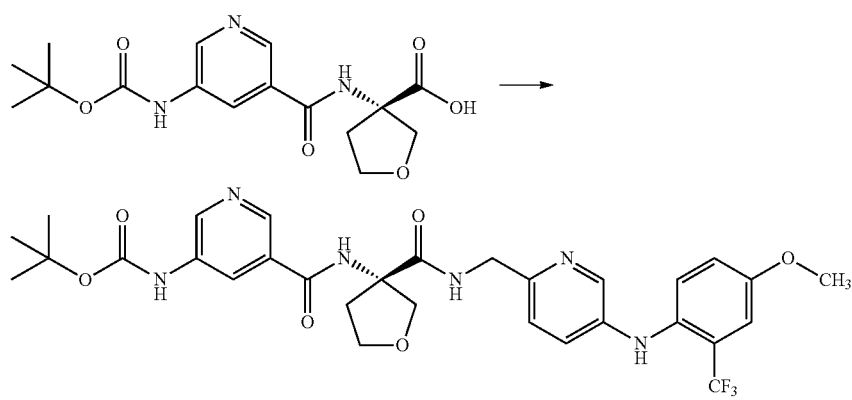

Analogously to Example 1e), (S)-3-[(5-tert-butoxycarbonylamino-pyridine-3-carbonyl)-amino]-tetrahydrofuran-3-carboxylic acid (product from Example 5d, 1.7 mmol) was reacted with (6-aminomethyl-pyridin-3-yl)-(4-methoxy-2-trifluoromethyl-phenyl)-amine (product from Example 5b, 1.7 mmol). The product was purified by chromatography (silica gel, dichloromethane with 0-10% methanol).

Yield: 69% of theory
$C_{30}H_{33}F_3N_6O_6$ (630.6)
Thin layer chromatograph (silica gel; dichloromethane/ethanol 9:1): $R_f$=0.46

5f) (S)-5-amino-N-(3-{[5-(4-methoxy-2-trifluoromethyl-phenylamino)-pyridin-2-ylmethyl]-carbamoyl}-tetrahydrofuran-3-yl)-nicotinamide tert-Butyl(S)-[5-(3-{[5-(4-methoxy-2-trifluoromethyl-phenylamino)-pyridin-2-ylmethyl]-carbamoyl}-tetrahydrofuran-3-ylcarbamoyl)-pyridin-3-yl]-carbamate (product from Example 5e, 1.2 mmol) was stirred with a 4N HCl solution in dioxane (20 mL) for two hours at ambient temperature. Then the mixture was evaporated to dryness, the residue was triturated with approx. 20 mL diethyl ether and suction filtered.

Yield: 82% of theory $C_{25}H_{25}F_3N_6O_4$ (530.5)

Mass spectrum (ESI): $[M+H]^+=531$ $[M-H]^-=529$

HPLC: $R_t=1.014$ min (method 3)

Example 6

(S)-5-amino-N-(3-{[3-chloro-5-(4-methoxy-2-trifluoromethyl-phenylamino)-pyridin-2-yl-methyl]-carbamoyl}-tetrahydrofuran-3-yl)-nicotinamide

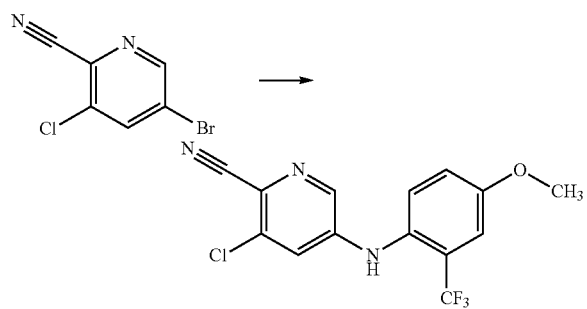

6a) 3-chloro-5-(4-methoxy-2-trifluoromethyl-phenylamino)-pyridin-2-carbonitrile

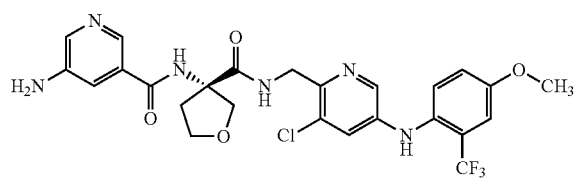

5-bromo-3-chloro-pyridine-2-carbonitrile (2.3 mmol) was reacted analogously to Example 1a) with 4-methoxy-2-trifluoroaniline (2.3 mmol). After chromatographic purification through silica gel (petroleum ether with 15 to 30% ethyl acetate) the product was obtained in a yield of 27% of theory.

$C_{14}H_9ClF_3N_3O$ (327.7)

Mass spectrum (ESI): $[M+H]^+=328$ $[M-H]^-=326$

HPLC: $R_t=1.558$ min (method 2)

6b) (6-aminomethyl-5-chloro-pyridin-3-yl)-(4-methoxy-2-trifluoromethyl-phenyl)-amine

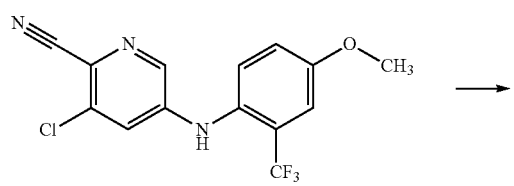

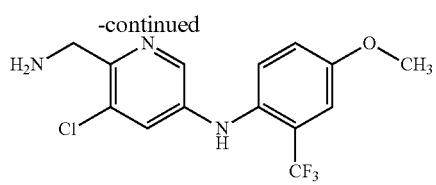

A solution of 3-chloro-5-(4-methoxy-2-trifluoromethyl-phenylamino)-pyridine-2-carbonitrile (0.64 mmol) in 10 mL ethanol and 0.1 mL hydrochloric acid (37%) was combined with 30 mg of Pd/charcoal (10%) and hydrogenated with stirring at ambient temperature. Then the catalyst was filtered off and the solution was evaporated down. The product thus obtained was reacted further without purification.

Yield: 99% of theory $C_{14}H_{13}ClF_3N_3O$ (331.7)

HPLC: $R_t=1.167$ min (method 2)

6c) (S)-5-amino-N-(3-{[3-chloro-5-(4-methoxy-2-trifluoromethyl-phenylamino)-pyridin-2-ylmethyl]-carbamoyl}-tetrahydrofuran-3-yl)-nicotinamide

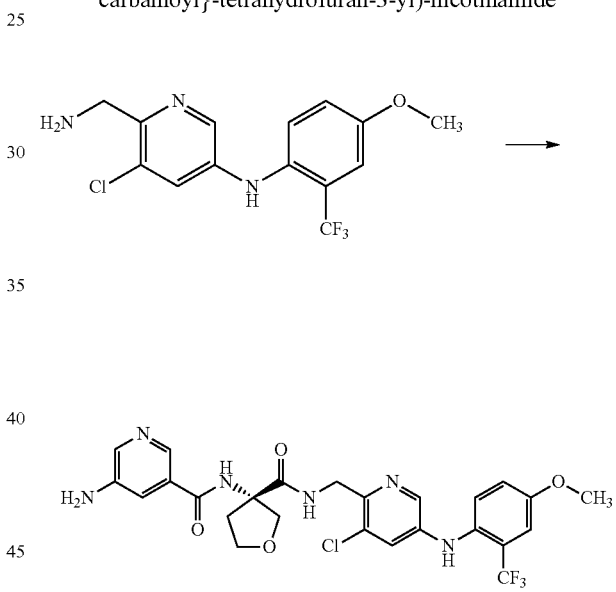

Analogously to Example 1e), (6-aminomethyl-5-chloro-pyridin-3-yl)-(4-methoxy-2-trifluoromethyl-phenyl)-amine (1.3 mmol) was reacted with (S)-3-[(5-amino-pyridin-3-carbonyl)-amino]-tetrahydrofuran-3-carboxylic acid (product from Example 2b, 1.3 mmol).

After chromatographic purification (silica gel, dichloromethane/methanol 9:1 with 3-8% ammonia) the product was obtained in a yield of 13% of theory.

$C_{25}H_{24}ClF_3N_6O_4$ (564.9)

$^1$H-NMR ($d_6$-DMSO): δ=2.27-2.46 (m, 2H); 3.78-3.88 (m, 2H); 3.85 (s, 3H); 3.94 (m, 1H); 4.23 (m, 1H); 4.24-4.38 (m, 2H); 5.49 (m 2H); 6.97 (d, 1H); 7.27-7.31 (m, 3H); 7.35-7.41 (m, 1H); 7.85 (d, 2H); 7.95 (m, 1H); 8.04 (d, 1H); 8.23 (s, 1H); 8.80 (s, 1H) ppm.

The following Examples describe pharmaceutical formulations which contain as active substance any desired compound of general formula I, without however restricting the scope of the present invention thereto:

Example I

Dry Ampoule with 75 mg of Active Compound Per 10 ml

Composition:

| | |
|---|---|
| Active compound | 75.0 mg |
| Mannitol | 500 mg |
| Water for injection | ad 10.0 ml |

Production:

Active compound and mannitol are dissolved in water. The charged ampoules are freeze dried. Water for injection is used to dissolve to give the solution ready for use.

Example II

Tablet with 50 mg of Active Compound

Composition:

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 9 mm.

Example III

Tablet with 350 mg of Active Compound

Composition:

| | |
|---|---|
| (1) Active compound | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 12 mm.

Example IV

Capsule with 50 mg of Active Compound

Composition:

| | |
|---|---|
| (1) Active compound | 50.0 mg |
| (2) Maize starch dried | 58.0 mg |
| (3) Lactose powdered | 50.0 mg |
| (4) Magnesium stearate | 2.0 mg |
| | 160.0 mg |

Production:

(1) is triturated with (3). This trituration is added to the mixture of (2) and (4) with vigorous mixing.

This powder mixture is packed into hard gelatine two-piece capsules of size 3 in a capsule-filling machine.

Example V

Capsules with 350 mg of Active Compound

Composition:

| | |
|---|---|
| (1) Active compound | 350.0 mg |
| (2) Maize starch dried | 46.0 mg |
| (3) Lactose powdered | 30.0 mg |
| (4) Magnesium stearate | 4.0 mg |
| | 430.0 mg |

Production:

(1) is triturated with (3). This trituration is added to the mixture of (2) and (4) with vigorous stirring.

This powder mixture is packed into hard gelatine two-piece capsules of size 0 in a capsule-filling machine.

Example VI

Suppositories with 100 mg of Active Compound 1 suppository comprises:

| | |
|---|---|
| Active compound | 100.0 mg |
| Polyethylene glycol (M.W. 1500) | 600.0 mg |
| Polyethylene glycol (M.W. 6000) | 460.0 mg |
| Polyethylene sorbitan monostearate | 840.0 mg |
| | 2000.0 mg |

The invention claimed is:

1. A compound of the formula I (I)

$R^1$—C(=O)—NH—[3-substituted oxolane]—C(=O)—NH—CH$_2$—[pyridine with X, $R^2$]—NH—[phenyl with OCH$_3$ and CF$_3$]

wherein
R¹ denotes a group selected from
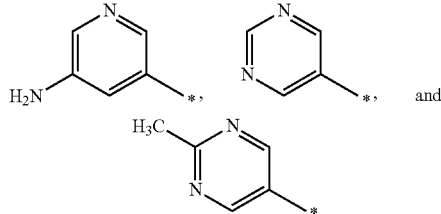
R² denotes H, Cl or F and
X denotes CH or N,
or a salt thereof.
2. A compound of the formula Ib
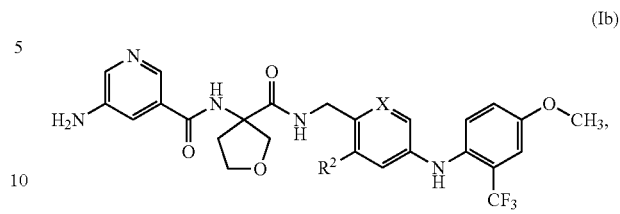
(Ib)
wherein
R² denotes H, Cl or F and
X denotes CH or N,
or a salt thereof.
3. A compound of the formula I according to claim 1, selected from the group consisting of:
| No. | Structure |
|---|---|
| (1) | 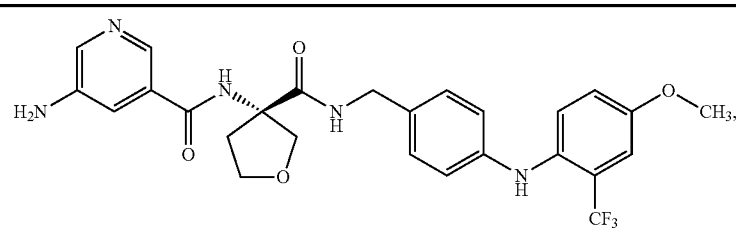 |
| (2) | 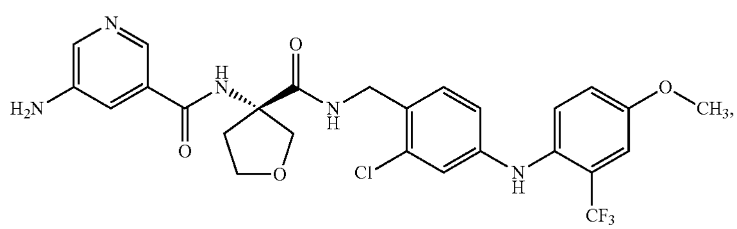 [SMILES: COc1ccc(Nc2ccc(CNC(=O)[C@]3(NC(=O)c4cncc(N)c4)CCOC3)c(Cl)c2)c(C(F)(F)F)c1] |
| (3) | 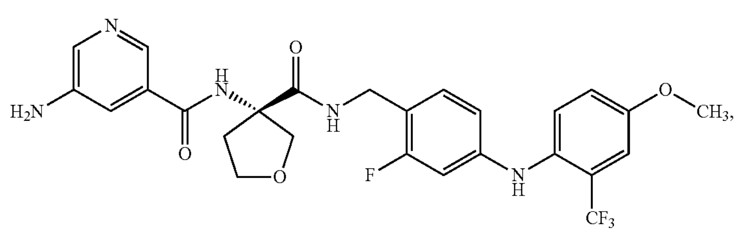 [SMILES: COc1ccc(Nc2ccc(CNC(=O)[C@]3(NC(=O)c4cncc(N)c4)CCOC3)c(F)c2)c(C(F)(F)F)c1] |
| (4) | 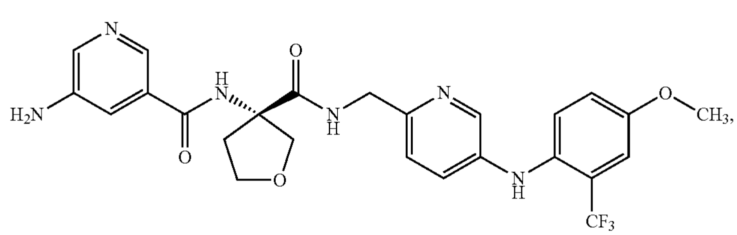 [SMILES: COc1ccc(Nc2ccc(CNC(=O)[C@]3(NC(=O)c4cncc(N)c4)CCOC3)nc2)c(C(F)(F)F)c1] |
| (5) | 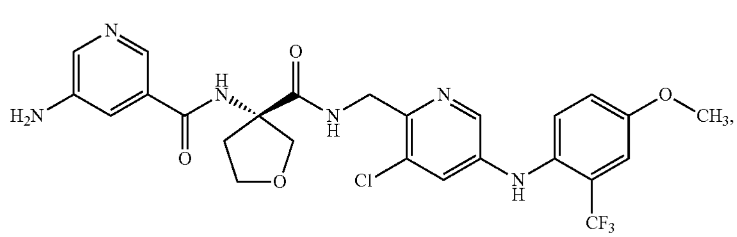 [SMILES: COc1ccc(Nc2cnc(CNC(=O)[C@]3(NC(=O)c4cncc(N)c4)CCOC3)c(Cl)c2)c(C(F)(F)F)c1] |

| No. | Structure |
|---|---|
| (6) | 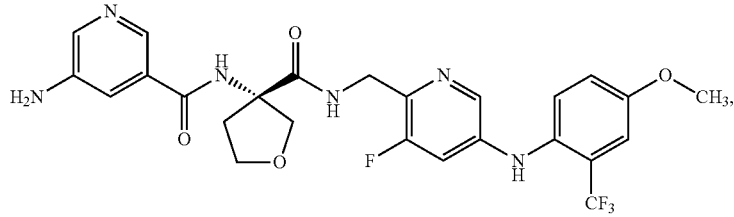 |
| (7) | 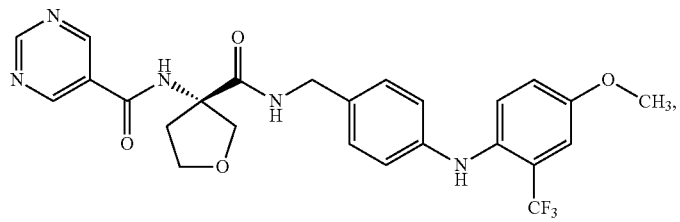 [SMILES: COc1ccc(Nc2ccc(CNC(=O)[C@]3(NC(=O)c4cncnc4)CCOC3)cc2)c(C(F)(F)F)c1] |
| (8) | 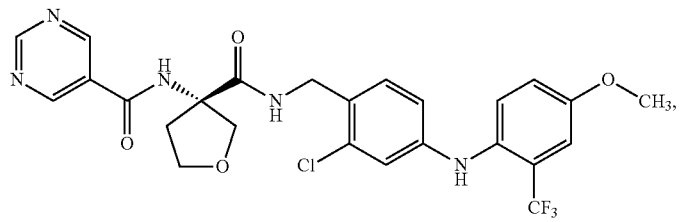 [SMILES: COc1ccc(Nc2ccc(CNC(=O)[C@]3(NC(=O)c4cncnc4)CCOC3)c(Cl)c2)c(C(F)(F)F)c1] |
| (9) | 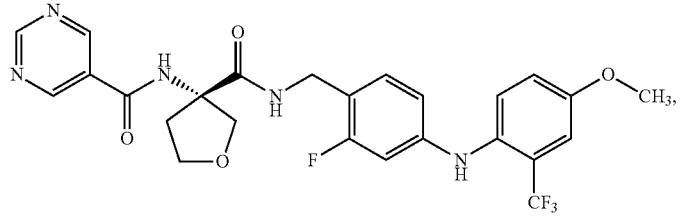 [SMILES: COc1ccc(Nc2ccc(CNC(=O)[C@]3(NC(=O)c4cncnc4)CCOC3)c(F)c2)c(C(F)(F)F)c1] |
| (10) | 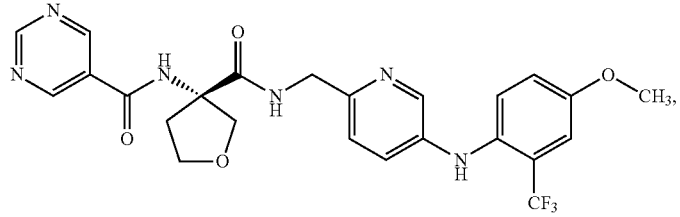 [SMILES: COc1ccc(Nc2ccc(CNC(=O)[C@]3(NC(=O)c4cncnc4)CCOC3)nc2)c(C(F)(F)F)c1] |
| (11) | 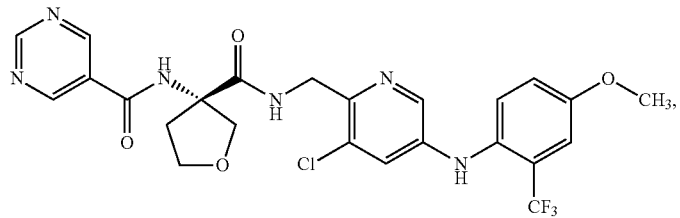 [SMILES: COc1ccc(Nc2cnc(CNC(=O)[C@]3(NC(=O)c4cncnc4)CCOC3)c(Cl)c2)c(C(F)(F)F)c1] |

| No. | Structure |
|---|---|
| (12) | *structure: pyrimidine-C(=O)-NH-[tetrahydrofuran-3-yl]-C(=O)-NH-CH₂-(5-fluoro-pyridin-2-yl, 5-NH-(4-methoxy-2-trifluoromethylphenyl))* |
| (13) | *structure: 2-methylpyrimidine-5-C(=O)-NH-[tetrahydrofuran-3-yl]-C(=O)-NH-CH₂-phenyl-NH-(4-methoxy-2-trifluoromethylphenyl)* |
| (14) | *structure: 2-methylpyrimidine-5-C(=O)-NH-[tetrahydrofuran-3-yl]-C(=O)-NH-CH₂-(2-chlorophenyl)-NH-(4-methoxy-2-trifluoromethylphenyl)* |
| (15) | *structure: 2-methylpyrimidine-5-C(=O)-NH-[tetrahydrofuran-3-yl]-C(=O)-NH-CH₂-(2-fluorophenyl)-NH-(4-methoxy-2-trifluoromethylphenyl)* |
| (16) | *structure: 2-methylpyrimidine-5-C(=O)-NH-[tetrahydrofuran-3-yl]-C(=O)-NH-CH₂-(pyridin-2-yl, 5-NH-(4-methoxy-2-trifluoromethylphenyl))* |
| (17) | *structure: 2-methylpyrimidine-5-C(=O)-NH-[tetrahydrofuran-3-yl]-C(=O)-NH-CH₂-(3-chloropyridin-2-yl, 5-NH-(4-methoxy-2-trifluoromethylphenyl))*, and |

| No. | Structure |
|---|---|
| (18) | 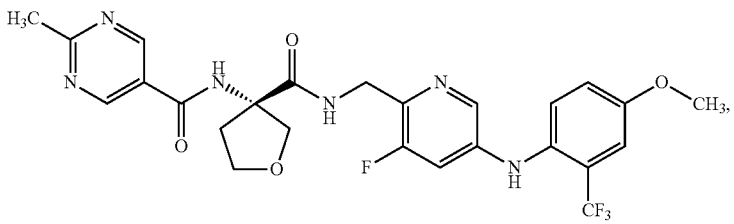 [SMILES: COc1ccc(Nc2cnc(CNC(=O)[C@]3(NC(=O)c4cnc(C)nc4)CCOC3)c(F)c2)c(C(F)(F)F)c1] | or a salt thereof.

4. A physiologically acceptable salt of a compound according to claim 1, 2 or 3.

5. A pharmaceutical composition comprising a compound according to claim 1 together with one or more inert carriers and/or diluents.

6. A method for treating pain caused by osteoarthritis which comprises administering to a host suffering from pain caused by osteoarthritis a therapeutically effective amount of a compound according to claim 1.

7. A compound of the formula Ic

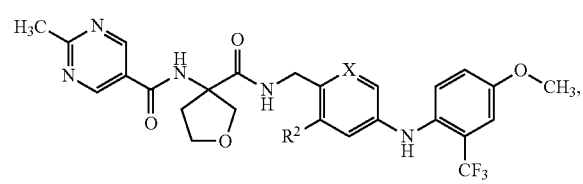

wherein
$R^2$ denotes H, Cl or F and
X denotes CH or N,
or a salt thereof.

8. A compound of the formula Id

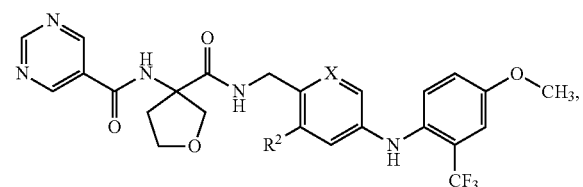

wherein
$R^2$ denotes H, Cl or F and
X denotes CH or N,
or a salt thereof.

9. The compound of the formula

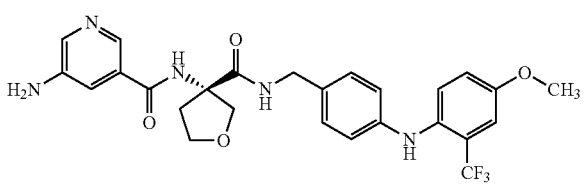 [SMILES: COc1ccc(Nc2ccc(CNC(=O)[C@]3(NC(=O)c4cncc(N)c4)CCOC3)cc2)c(C(F)(F)F)c1]

or a pharmaceutically acceptable salt thereof.

10. The compound of the formula

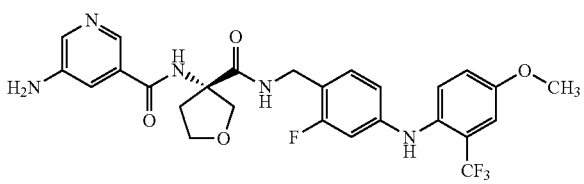 [SMILES: COc1ccc(Nc2ccc(CNC(=O)[C@]3(NC(=O)c4cncc(N)c4)CCOC3)c(F)c2)c(C(F)(F)F)c1]

or a pharmaceutically acceptable salt thereof.

11. The compound of the formula

or a pharmaceutically acceptable salt thereof.

12. The compound of the formula or a pharmaceutically acceptable salt thereof.

13. The compound of the formula

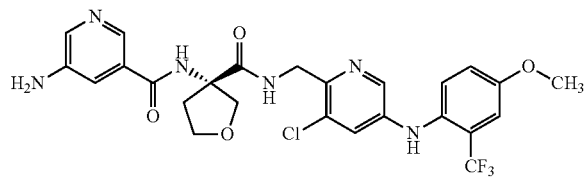 [SMILES: COc1ccc(Nc2cnc(CNC(=O)[C@]3(NC(=O)c4cncc(N)c4)CCOC3)c(Cl)c2)c(C(F)(F)F)c1]

or a pharmaceutically acceptable salt thereof.

14. The compound of the formula

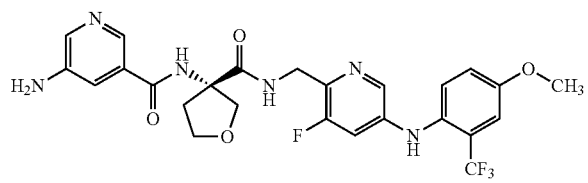 [SMILES: COc1ccc(Nc2cnc(CNC(=O)[C@]3(NC(=O)c4cncc(N)c4)CCOC3)c(F)c2)c(C(F)(F)F)c1]

or a pharmaceutically acceptable salt thereof.

15. The compound of the formula

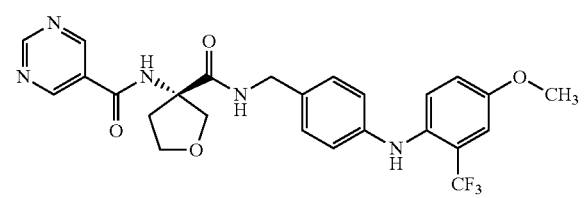

or a pharmaceutically acceptable salt thereof.

16. The compound of the formula

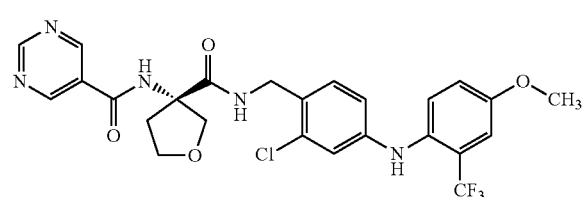

or a pharmaceutically acceptable salt thereof.

17. The compound of the formula

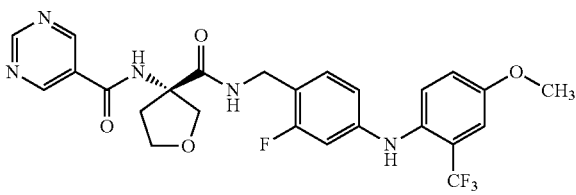 [SMILES: COc1ccc(Nc2ccc(CNC(=O)[C@]3(NC(=O)c4cncnc4)CCOC3)c(F)c2)c(C(F)(F)F)c1]

or a pharmaceutically acceptable salt thereof.

18. The compound of the formula

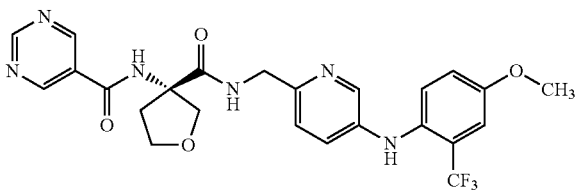 [SMILES: COc1ccc(Nc2ccc(CNC(=O)[C@]3(NC(=O)c4cncnc4)CCOC3)nc2)c(C(F)(F)F)c1]

or a pharmaceutically acceptable salt thereof.

19. The compound of the formula

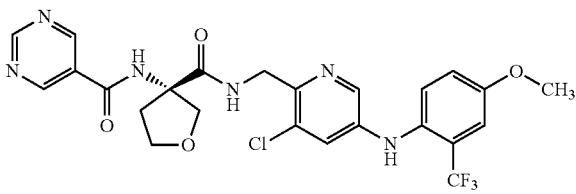 [SMILES: COc1ccc(Nc2cnc(CNC(=O)[C@]3(NC(=O)c4cncnc4)CCOC3)c(Cl)c2)c(C(F)(F)F)c1]

or a pharmaceutically acceptable salt thereof.

20. The compound of the formula

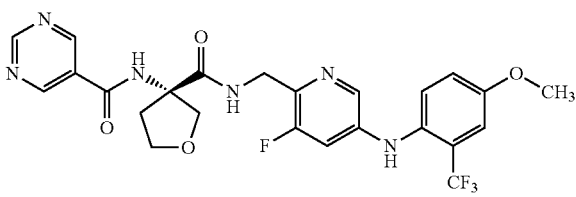 [SMILES: COc1ccc(Nc2cnc(CNC(=O)[C@]3(NC(=O)c4cncnc4)CCOC3)c(F)c2)c(C(F)(F)F)c1]

or a pharmaceutically acceptable salt thereof.

* * * * *